(12) United States Patent
Van Dyke

(10) Patent No.: US 8,258,093 B2
(45) Date of Patent: *Sep. 4, 2012

(54) WOUND HEALING COMPOSITIONS CONTAINING KERATIN BIOMATERIALS

(75) Inventor: Mark E. Van Dyke, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/241,552

(22) Filed: Sep. 23, 2011

(65) Prior Publication Data

US 2012/0009237 A1 Jan. 12, 2012

Related U.S. Application Data

(60) Division of application No. 12/104,682, filed on Apr. 17, 2008, which is a continuation-in-part of application No. 11/676,072, filed on Feb. 16, 2007.

(60) Provisional application No. 60/774,442, filed on Feb. 17, 2006, provisional application No. 60/774,587, filed on Feb. 17, 2006, provisional application No. 60/774,920, filed on Feb. 17, 2006.

(51) Int. Cl.
*C07K 14/00* (2006.01)

(52) U.S. Cl. .......................... 514/1; 530/350

(58) Field of Classification Search ....... 514/1; 530/350
See application file for complete search history.

(56) References Cited

U.S. PATENT DOCUMENTS

| | | |
|---|---|---|
| 922,692 A | 5/1909 | Goldsmith |
| 926,999 A | 7/1909 | Neuberg |
| 960,914 A | 6/1910 | Heinemann |
| 1,214,299 A | 1/1917 | Grosvenor et al. |
| 2,236,921 A | 4/1941 | Schollkopf et al. |
| 2,413,983 A | 1/1947 | Lustig et al. |
| 2,434,688 A | 1/1948 | Evans |
| 2,445,028 A | 7/1948 | Jones et al. |
| 2,517,572 A | 8/1950 | Jones et al. |
| 2,814,851 A | 12/1957 | Hervey |
| 3,033,755 A | 5/1962 | Jacobi |
| 3,464,825 A | 9/1969 | Anker |
| 3,642,498 A | 2/1972 | Anker |
| 3,655,416 A | 4/1972 | Vinson et al. |
| 4,178,361 A | 12/1979 | Cohen et al. |
| 4,357,274 A | 11/1982 | Werner |
| 4,423,032 A | 12/1983 | Abe et al. |
| 4,495,173 A | 1/1985 | Matsunaga et al. |
| 4,570,629 A | 2/1986 | Widra |
| 4,751,074 A | 6/1988 | Matsunaga et al. |
| 4,822,349 A | 4/1989 | Hursey et al. |
| 4,895,722 A | 1/1990 | Abe et al. |
| 4,959,213 A | 9/1990 | Brod et al. |
| 5,047,249 A | 9/1991 | Rothman et al. |
| 5,300,285 A | 4/1994 | Halloran et al. |
| 5,320,796 A | 6/1994 | Harashima et al. |
| 5,358,935 A | 10/1994 | Smith et al. |
| 5,583,126 A | 12/1996 | Daynes et al. |
| 5,634,945 A | 6/1997 | Pernia et al. |
| 5,679,819 A | 10/1997 | Jones et al. |
| 5,691,203 A | 11/1997 | Katsuen et al. |
| 5,707,972 A | 1/1998 | Shimizu |
| 5,763,583 A | 6/1998 | Arai et al. |
| 5,840,309 A | 11/1998 | Herstein et al. |
| 5,932,552 A | 8/1999 | Blanchard et al. |
| 5,948,432 A | 9/1999 | Timmons et al. |
| 6,063,757 A | 5/2000 | Urso |
| 6,110,487 A | 8/2000 | Timmons et al. |
| 6,124,265 A | 9/2000 | Timmons et al. |
| 6,159,495 A | 12/2000 | Timmons et al. |
| 6,159,496 A | 12/2000 | Blanchard et al. |
| 6,165,496 A | 12/2000 | Timmons et al. |
| 6,268,454 B1 | 7/2001 | Song et al. |
| 6,270,791 B1 | 8/2001 | Van Dyke et al. |
| 6,270,793 B1 | 8/2001 | Van Dyke et al. |
| 6,274,155 B1 | 8/2001 | Van Dyke et al. |
| 6,274,163 B1 | 8/2001 | Blanchard et al. |
| 6,316,598 B1 | 11/2001 | Van Dyke et al. |
| 6,371,984 B1 | 4/2002 | Van Dyke et al. |
| 6,379,690 B2 | 4/2002 | Blanchard et al. |
| 6,432,435 B1 | 8/2002 | Timmons et al. |
| 6,461,628 B1 | 10/2002 | Blanchard et al. |
| 6,544,548 B1 | 4/2003 | Siller-Jackson et al. |
| 6,562,326 B1 | 5/2003 | Miller |
| 6,673,603 B2 | 1/2004 | Baetge et al. |
| 6,746,836 B1 | 6/2004 | Widra |

(Continued)

FOREIGN PATENT DOCUMENTS

DE     184915     12/1905

(Continued)

OTHER PUBLICATIONS

Van Dyke ME. Abstracts of Papers American Chemical Society, 224th National Meeting of the American Chemical Society held in Boston, MA Aug. 18-22, 2002, pages unknown.

Alam HB, Burris D, DaCorta JA, Rhee P. Hemorrhage control in the battlefield: role of new hemostatic agents *Military Medicine* 2005;170(1):63-69.

Lee SJ, Van Dyke ME. Tissue engineering scaffolds from self-assembled human hair keratins. *Polym Prep* 2005;46(1):112.

Pusateri AE, Modrow HE, Harris RA, Holcomb JB, Hess JR, Mosebar RH, Reid TJ, Nelson JH, Goodwin CW, Fitzpatrick GM, McManus AT, Zolock DT, Sondeen JL, Cornum RL, Martinez RS. Advanced hemostatic dressing development program: animal model selection criteria and results of a study of nine hemostatic dressings in a model of severe large venous hemorrhage and hepatic injury in swine. *J. Trauma* 2003;55(3):518-26.

(Continued)

*Primary Examiner* — Karen Cochrane Carlson

(74) *Attorney, Agent, or Firm* — Myers Bigel Sibley & Sajovec, P.A.

(57) ABSTRACT

Disclosed are keratin preparations for use in medical applications. Methods of treating wounds are provided, wherein keratin preparations are applied to the wound in a treatment effective amount. Methods of treating burn wounds are also provided. Surgical or paramedic aids are provided, comprising a substrate with keratin preparations provided thereon. Kits comprising keratin derivatives packaged in sterile form are also provided.

28 Claims, 5 Drawing Sheets

U.S. PATENT DOCUMENTS

| | | |
|---|---|---|
| 6,783,546 B2 | 8/2004 | Zucherman et al. |
| 7,148,327 B2 | 12/2006 | Kelly et al. |
| 2001/0047082 A1 | 11/2001 | Van Dyke et al. |
| 2003/0228353 A1 | 12/2003 | Cowsar |
| 2004/0076599 A1 | 4/2004 | Siller-Jackson et al. |
| 2006/0051732 A1 | 3/2006 | Van Dyke |
| 2007/0166348 A1 | 7/2007 | Van Dyke |
| 2007/0298070 A1 | 12/2007 | Van Dyke |

FOREIGN PATENT DOCUMENTS

| | | |
|---|---|---|
| DE | 22643 | 10/1907 |
| EP | 0 454 600 A1 | 4/1991 |
| EP | 0468797 A2 | 1/1992 |
| EP | 0 540 357 A2 | 5/1993 |
| GB | 531446 A | 1/1941 |
| GB | 2 241 253 A | 8/1991 |
| JP | 52-148581 A | 12/1977 |
| JP | 53-016091 A | 2/1978 |
| JP | 54-137064 A | 10/1979 |
| JP | 55-051095 A | 4/1980 |
| JP | 56-030909 A | 3/1981 |
| JP | Sho 55-98256 | 2/1982 |
| JP | S57-109797 | 7/1982 |
| JP | 1-174528 | 7/1989 |
| JP | 2-051533 A | 2/1990 |
| JP | 3-011099 A | 1/1991 |
| JP | 4-082561 A | 3/1992 |
| JP | 4-091138 A | 3/1992 |
| JP | Hei 4-189833 | 7/1992 |
| JP | 5-285374 A | 11/1993 |
| JP | 5-285375 A | 11/1993 |
| JP | 5-320358 A | 12/1993 |
| JP | 6-100600 A | 4/1994 |
| JP | 6-116300 A | 4/1994 |
| JP | 6-336499 A | 12/1994 |
| JP | 9-227565 A | 9/1997 |
| JP | 10-291998 A | 11/1998 |
| JP | 10-291999 A | 11/1998 |
| JP | 10-337466 | 12/1998 |
| JP | 2000-191792 A | 7/2000 |
| JP | 2001-087754 A | 4/2001 |
| JP | 2001-114647 A | 4/2001 |
| NL | 51000577 | 12/1941 |
| RU | 2 106 154 C1 | 3/1998 |
| RU | 2 108 079 C1 | 4/1998 |
| WO | WO 91-02538 A1 | 3/1991 |
| WO | WO 93/10827 A1 | 6/1993 |
| WO | WO 93/12819 A1 | 7/1993 |
| WO | WO 98/08550 A1 | 3/1998 |
| WO | WO 99/26570 A1 | 6/1999 |
| WO | WO 99/26595 A1 | 6/1999 |
| WO | WO 99/51175 A1 | 10/1999 |
| WO | WO 00/76437 A1 | 12/2000 |
| WO | WO 00-76437 A1 | 12/2000 |
| WO | WO 01/19283 A2 | 3/2001 |
| WO | WO 01/19305 A1 | 3/2001 |
| WO | WO 01/64033 A2 | 9/2001 |
| WO | WO 02/45508 A1 | 6/2002 |
| WO | WO 03/011894 A1 | 2/2003 |
| WO | WO 03/064449 A2 | 8/2003 |
| WO | WO 03/086491 A2 | 10/2003 |
| WO | WO 2004/011052 A1 | 2/2004 |
| WO | WO 2007/001339 A2 | 1/2007 |
| WO | WO 2007/098053 | 8/2007 |

OTHER PUBLICATIONS

Mitsui S, Ohuchi A, Hotta M, Tsuboi R, Ogawa H. Genes for a range or growth factors and cyclin-dependent kinase inhibitors are expressed by isolated human hair follicles. *British J Dermatol.* 1997:137:693-698.

Crewther WG et al., *The Chemistry of Keratins*. Anfinsen CB Jr et al., editors. Advances in Protein Chemistry 1965. Academic Press. New York:191-346.

O'Donnell IJ and Thompson EOP. Studies on oxidized wool IV. Fractionation of proteins extracted from wool on DEAE-cellulose using buffers containing 8M urea. *Aust. J. Biol. Sci.* 1961;14:461-474.

Goddard DR and Michaelis L. A study on keratin. *J Biol Chem* 1934;106:605-14.

Thompson et al., Studies on Reduced Wool, *Aust. J. Biol. Sci.* 15:757-68 (1962).

Yamauchi, The development of Keratin: Characteristics of Polymer Films. Fragrance J. 21(5):62-67 (1993). (English Translation of Entire Document).

Marionnet C et al. Interactions between fibroblasts and keratinocytes in morphogenesis of dermal epidermal junction in a model of reconstructed skin. J. Inv. Derm. 2006;126:971-979.

Ward RS and Saffle JR. Topical agents in burn and wound care. Physical Therapy. Jun. 1995;75(6):526-38.

International Search Report and Written Opinion, PCT/US07/04283, mailed Oct. 8, 2008.

International Search Report and Written Opinion, PCT/US2008/004984, mailed Dec. 23, 2008.

Lee KY et al. Effect of surface properties on the antithrombogenicity of silk fibroin/S-carboxymethyl kerateine blend films. J. Biomater. Sci. Polymer Edn. 1998; 9(9): 905-914.

Supplementary European Search Report, EP 07751069, mailed Aug. 17, 2010.

European Examination Report, EP 08743024, mailed Aug. 31, 2010.

Steinert PM and Idler WW. The polypeptide composition of bovine epidermal alpha-keratin. Biochem. J. 1975; 151: 603-614.

Sayers Z et al. Structure and assembly of calf hoof keratin filaments. Journal of Structural Biology. 1990; 103: 212-224.

Noishiki Y et al. Application of denatured wool keratin derivatives to an antithrombogenic biomaterial—a vascular graft coated with a heparinised keratin derivative. Kobunshi Rombunshu. Apr. 1982; 39(4): 221-227.

Israel Search Report, Israeli Patent Application No. 201,425, mailed Oct. 11, 2011.

Lindley, H.; et al; "The preparation and properties of a group of proteins from the high sulphur fraction of wool"; Biochemical Journal; vol. 128, No. 4, 1972, pp. 859-867.

Lindley, H.; et al; "The reactivity of the disulphide bonds of wool"; Biochemical Journal; vol. 139, No. 3, 1974, pp. 515-523.

Lindley, H.; Haylett, T.; "Occurance of the Cys-Cys Sequence in keratins."; Journal Molecular Biology; vol. 30, 1967, pp. 63-67.

Lindley,, H.; et al; "Disulphide interchange reactions involving cyclosystine and their relevance to problems of α-keratin structure" Biochemical Journal; vol. 108, No. 4, 1968, pp. 701-703.

Lissizin, Th.; "Behavior of keratin sulfur and cystin sulfur, in the oxidation of these proteins by potassium permanganate." Biochemistry Bulletin vol. 4, 1915, pp. 18-23.

Lissizin, Th.; "The oxidation products of keratin by oxidation with permanganate." Z. Physiology Chem. vol. 173, 1928, pp. 309-311.

Liu, S.M.; et al; "Transsulfuration, protein synthesis rate and follicle mRNA in the skin of young Merino lambs in response to infusions of methionine and serine."; British Journal of Nutrition; vol. 83, No. 4, 2000, pp. 401-409.

Lotay, S.S.; Speakman, P.T.; "Three-chain merokeratin from wool may be a fragment of the microfibril component macromolecule"; Nature; vol. 265, 1977, pp. 274-277.

Lyons, K.M.; et al.; "Patterns of expression of murine Vgr-1 and BMP-2a RNA suggest that transforming growth factor-β-like genes coordinately regulate aspects of embryonic development." Genes & Development; vol. 3, 1989, pp. 1657-1668.

Mack, J.W.; Torchia, D.A.; Steinert, P.M.; "Solid-State NMR Studies of the Dynamics and Stucture of Mouse Keratin Intermediate Filaments."; Biochemistry; vol. 27, No. 15. 1988, pp. 5418-5426.

MacKinnon, P.J.; et al; "An ultrahigh-sulphur keratin gene of the human hair cuticle is located at 11q13 and cross-hybridizes with sequences at 11p15."; Mammalian Genome; vol. 1, 1991 pp. 53-56.

MacLaren, J.A.; "The extent of reduction of wool proteins by thiols." The Australian Journal of Chemistry; vol. 15,No. 4, 1962, pp. 824-831.

Marikovsky, M.; et al.; "Appearance of heparin-binding EGF-like growth factor in wound fluid as a response to injury."; Proceedings of the National Academy of Sciences, USA; vol. 90, 1993, pp. 3889-3893.

Marshall, R.C. et al; "High-sulfur proteins in mammalian keratins: a possible aid in classification."; Australian Journal of Zoology; vol. 25, No. 1, 1977, pp. 121-132.

Marshall, R.C.; "Analysis of the proteins from single wool fibers by two-dimensional polyacrylamide-gel electrophoresis."; Textile Research Journal; vol. 51, No. 2, 1981, pp. 106-108.

Marshall, R.C.; "Changes in wool low-sulphur and high-sulphur protein-components following chemical defleecing."; Textile Research Journal; vol. 51, No. 6, 1981, pp. 384-388.

Marshall, R.C.; "Characterization of the proteins of human hair and nail by electrophoresis."; Journal of Investigative Dermatology; vol. 80, No. 6, 1983, pp. 519-524.

Marshall, R.C.; "Cysteine-rich proteins of mouse hair."; Proceedings of the Australian Biochemical Society; vol. 8, 1975, pp. 4.

Marshall, R.C.; "Forensic identification of hairs by electrophoresis."; Journal of the Forensic Society; vol. 24, No. 4, 1984, pp. 330.

Marshall, R.C.; "Genetic variation in the proteins of human nail."; Journal of Investigative Dermatology; vol. 75, No. 3, 1980, pp. 264-269.

Marshall, R.C.; Blagrove, R.J.; "Successful isoelectric focusing of wool low-sulphur proteins."; Journal of Chromatography; vol. 172, 1979, pp. 351-356.

Marshall, R.C.; et al; "An investigation of the relationship of wool textile properties to fiber protein composition."; Proceedings of the International Wool Textile Research Conf.; vol. 1, 1990, pp. 266-275.

Marshall, R.C.; et al; "Examination of proteins of wool cuticle by two-dimensional gel-electrophoresis."; Textile Research Journal; vol. 56, No. 12, 1986, pp. 772-774.

Marshall, R.C.; et al; "High sulphur proteins and α-keratins II.* Isolatioin and partial characterization of purified components from mouse hair."; Australian Journal of Biological Sciences.; vol. 29, 1976, pp. 11-20.

Marshall, R.C.; et al; "High sulphur proteins from α-keratins I. Heterogeneity of the proteins from mouse hair."; Australian Journal of Biological Sciences; vol. 29, 1976, pp. 1-10.

Marshall, R.C.; et al; "Possible identification of specialty fibers γ electrophoresis."; Textile Research Journal; vol. 54, No. 2, 1984, pp. 126-128.

Marshall, R.C.; et al; "Protein changes after short thermal treatments of wool fibrics."; Textile Research Journal; vol. 53, No. 12, 1983, pp. 792-794.

Marshall, R.C.; et al; "Sequence studies of wool proteins rich in glycine and aromatic residues."; Proceedings of the Australian Biochemical Society; vol. 12, 1979, pp. 12.

Marshall, R.C.; Gillespie, J.M.; "The keratin proteins of wool, horn and hoof from sheep." Australian Journal of Biological Sciences; vol. 30, 1977, pp. 389-400.

Marshall, R.C; et al.; "Heterogeneity and incomplete disulfide reduction in the high sulphur proteins of wool." Australian Journal of Biological Sciences; vol. 31, 1978, pp. 219-229.

Martin, P. "Wound Healing—Aiming for Perfect Skin Regeneration."; Science; vol. 276, 1997, pp. 75-81.

Mason, E.D.; et al.; "Dorsal midline fate in Drosophila embryos requires twisted gastrulation, a gene encoding a secreted protein related to human connective tissue growth factor." Genes and Development vol. 8, 1994, pp. 1489-1501.

Matsunaga, A.; et al; "Studies on the chemical property of human hair keratin. Part I. Fractionation and amino acid composition of human hair keratin solubilized by performic acid oxidation."; Hikaku Kagaku; vol. 27(1), 1981, pp. 21-29.

Mazzoni, M.C.; et al; "Blood and plasma viscocity and microvascular function in hemodilution. A perspective from LaJolla, California."; European Surgical Research; vol. 34, (1-2), 2002 Ref. 35.

McCloghry, C.E.; et al; "Wool follicles initiate, develop and produce fibres in ovine foetal skin grafts."; Proceedings of the Australian Society of Animal Production; vol. 18, 1990, pp. 518.

McMillin, D.R.; Holwerda, R.A.; Gray, H.B.; "Preparation and spectroscopic studies of cobalt (II) stellacyanin"; Proceedings of the National Academy of Sciences; vol. 71, No. 4, 1974, pp. 1339-1341.

McMillin, D.R.; Rosenberg, R.C.; Gray, H.B.; "Preparation and spectroscopic studies of cobalt (II) derivatives of blue copper proteins."; Proceedings of the National Academy of Sciences; vol. 71, No. 12, 1974, pp. 4760-4762.

Mies, H.H.; et al.; "Preparation of soluble proteins from wool."; Leder; vol. 39, 1988, pp. 1-9.

Mies, H.H.; Zahn, H.; "Chromatographic and electrophoretic investigations of the properties of unprotected low-sulphur wool keratins."; Journal of Chromatography; vol. 405, 1987, pp. 365-370.

Mitsui, S.; Ohuchi, A; Hotta, M.; Tsuboi, R.; Ogawa, H.; "Genes for a range of growth factors and cyclin-dependent kinase inhibitors are expressed by isolated human hair follicles." British Journal of Dermatology; vol. 137, 1997, pp. 693-698.

Miwa, M.; et al; "Effects of fiber length on the tensile strength of epoxy/glass fiber and polyester/glass fiber composites." Journal of Applied Polymer Science; vol. 25, 1980, pp. 795-807.

Miyamoto, T.: et al; "Sorption Behavior of Heavy Metal Ions on S-Subtituted Kerateine Gels." Institute for Chemical Research; vol. 34, No. 10, 1978, pp. T-447-T-454.

Moll, R.; et al.; "The catalog of humans cytokeratins: Patterns of expression in normal epithelia, tumors and cultured cells." Cell; vol. 31, 1982, pp. 11-24.

Mueller, R.V.; et al.; "The effect of insulinlike growth factor I on wound healing variables and macrophages in rats." Archives of Surgery; vol. 129, 1994, pp. 262-265.

Nakamura, A.; et al; "Cysteine-containing oligopepetide model complexes of iron-sulfur proteins."; Advances in Inorganic Chemistry; vol. 33 1989, pp. 39-67.

Nakamura, Y.; et al; "Cystine in wool. Relation between sulfhydryl group and supercontraction." Sen-i Gakkaishi, vol. 16, 1960, pp. 852-858.

Nancarrow, M.J. et al; "Expression of ornithine decarboxylase during embryonic development of wool follicles."; Experimental Dermatology; vol. 8, 1999, pp. 362-368.

Noishiki, Y.; et al; "Application of denatured wool keratin derivatives to an antithrombogenic biomaterial. Vascular graft coated with a heparinized keratin derivative."; Kobunshi Ronbunshu; vol. 39(4), 1982, pp. 221-227.

Norman, J.A.T.; et al; "Reversible complexes for the recovery of dioxygen."; Procedings of the Annual IUCCP Symposium; 1987, pp. 107-125.

Okamoto, S.; "Formation of films from some proteins."; Nippon Shokuhin Kogyo Gakkaishi; vol. 24(1), 1977, pp. 40-50.

O'Shea, J.M.; et al; "The effect of ultrasonic irradiation on proteins." Australian Journal of Biological Sciences; vol. 26,1973, pp. 583-590.

Osterberg, R.; "Metal complexes of peptides."; Metal Catalog Lipid Oxidation; Sv. Inst. Konserveringsforsk, Symposium, Goteberg Sweden, 1967, pp. 119-127.

Panteleyev, A.A.; et al.; "Hair follicle predetermination."; Journal of Cell Science; vol. 114, 2001, pp. 3419-3431.

Parry, D.A.D.; et al; "Fibrous proteins: Scientific, Industrial and Medical aspects."; An Academic Press Fast Publication; vol. 1, 1979, pp. 1-132.

Parry, D.A.D.; et al; "Structure of α-keratin: Structural implication of the amino acid sequences of the type I and type II chain segments."; Journal of Molecular Biology; vol. 113, 1977, pp. 449-454.

Pauling, L.; Corey, R.B.; "The structure of feather rachis keratin." Proceedings of the National Academy of Sciences; vol. 37,No. 5, 1951, pp. 256-261.

Pauling, L.; Corey, R.B.; "The structure of hair, muscle, and related proteins."; Proceedings of the National Academy of Sciences; vol. 37, No. 5, 1951, pp. 261-271.

Peters, L.; "Affinity of ions for keratin."; Journal of Textile Institute; vol. 58, No. 4, 1967, pp. 179-180.

Peus, D., et al.; "Growth factors in hair organ development and the hair growth cycle." Dermatologic Clinins; vol. 14, No. 4, 1996, pp. 559-572.

Philpott, M.P.; et al.; "Whole hair follicle culture." Dermatologic Clinics; vol. 14, No. 4, 1996, pp. 595-607.

Powell, B.C.; "The keratin proteins and genes of wool and hair"; Wool Technology and Sheep Breeding; vol. 44, No. 2, 1996, pp. 100-118.

Powell, B.C.; et al; "The Notch signalling pathway in hair growth."; Mechanisms of Development; vol. 78, 1988, pp. 189-192.

Powell, B.C.; et al; "Characterization of a gene encoding a cysteine-rich keratin associated protein synthesized late in rabbit hair follicle differentiation."; Differentiation; vol. 58, 1995, pp. 227-232.

Powell, B.C.; et al; "Characterization of hair (wool) keratin intermediate filament gene domain."; Journal of Investigative Dermatology; vol. 102, 1994, pp. 171-177.

Powell, B.C.; et al; "Mammalian keratin gene families: organization of genes coding for the B2 high sulphur proteins of sheep wool."; Nucleic Acids Research; vol. 11, 1983, pp. 5327-5346.

Powell, B.C.; et al; "Regulation of Keratin Gene Expression in Hair Follicle Differentiation." Annals New York Academy of Sciences; vol. 642, 1991, pp. 1-20.

Powell, B.C.; et al; "The role of keratin proteins and their genes in the growth, structure and properties of hair."; EXS; vol. 78, 1997, pp. 59-148 Ref: 284.

Powell, B.C.; et al; "Transgenic sheep and wool growth: possibilities and current status."; Reproduction, Fertility, and Development; vol. 6, 1994, pp. 615-623.

Powell, B.C.; Kemp, D.J.; Partington, G.A.; Gibbs, P.E.M.; Rogers, G.E.; "Control of feather keratin synthesis by the availability of keratin mRNA."; Biochemical and Biophysical research Communications; vol. 68, No. 4, 1976, pp. 1263-1271.

Powell, B.C.; Rodgers, G.E.; "Cyclic hair-loss and regrowth in the transgenic mice overexpressing and intermediate filament gene."; The EMBO Journal vol. 9, No. 5, 1990, pp. 1485-1493.

Rana, T.M.; et al; "Specific cleavage of a protein by an attached iron chelate."; Journal of the American Chemical Society; vol. 112 (6), 1990, pp. 2457-2458.

Randall, V.A.; "The use of dermal papilla cells in studies of normal and abnormal hair follicle biology."; Dermatologic Clinics; vol. 14, No. 4 1996 pp. 585-594.

Ranford, J.D.; et al; "Matallodrugs. The role of thiolate proteins and metal-thiolate complexes."; Metallothioneins, Conference General Review; 1992, pp. 408-435.

Ranshoff, S.; et al; "Synthesis and characterization of new dioxygen carriers: a reexamination of the fly-over ligand system"; Inorganic Chemistry; vol. 29(16), 1990, pp. 2945-2947.

Raphael, K.A.; et al; "Protein and amino acid composition of hair from mice carrying the naked (N) gene."; Genetic Research, vol. 44, No. 1, 1984, pp. 29-38.

Rappolee, D.A.; et al.; "Wound macrophages express TGF-α and other growth factors in vivo: Analysis by mRNA phenotyping."; Science; vol. 241, 1988, pp. 708-712.

Rau, H.K; Snigula, H.; Struck, A.; Robert, B.; Scheer, H.; Haehnel, W.; "Design, synthesis and properties of synthetic chlorophyll proteins."; European Journal of Biochemistry; vol. 268, 2001, pp. 3284-3295.

Reis, P.J.; "Influence of dietary protein and methionine on the sulphur content and growth rate of wool in the millk fed lambs" Australian Journal of Biological Science; vol. 23, No. 1, 1970, pp. 193-200.

Reis, P.J.; "The growth and composition of wool—III. Variations in the sulphur content of wool."; Australian Journal of Biological Sciences; vol. 18, 1965, pp. 671-687.

Reis, P.J.; "The growth and composition of wool. IV. The differential response of growth and of sulphur content of wool to the level of sulphur containing amino acids given per abomasum" Australian Journal of Biological Science; vol. 20, No. 4, 1967, pp. 809-825.

Reis, P.J.; et al; "The utilization of abomasal supplements of proteins and amino acids by sheep with special reference to wool growth"; Australian Journal of Biological Sciences; vol. 25, 1972, pp. 1057-1071.

Reis, P.J.; et al; "The growth and composition of wool."; Australian Journal of Biological Sciences; vol. 18, No. 3, 1965, pp. 671-687.

Reis, P.J.; et al; "The influence of abomasal and intervenous supplements of sulphur containing amino acids on wool growth rate"; Australian Journal of Biological Sciences; vol. 26, No. 1, 1973, pp. 249-258.

Reis, P.J.; et al; "The nutritional control of the growth and properties of mohair and wool fibers: a comparative review"; Journal of Animal Science; vol. 72, No. 7, 1994, pp. 1899-1907.

Reis, P.J.; Gillespie, J.M.; "Effects of phhenylalanine and the analogues of methionine and phenylalanine on the composition of wool and mouse hair."Australian Journal of Biological Sciences; vol. 38, No. 2 pp. 151-163.

Reis, P.J.; Tunks, D.A.; Williams, O.B.; Williams, A. J.; "A relationship between sulphur content of wool and wool production by merino sheep."; Australian Journal of Biological Sciences; vol. 20, 1967, pp. 153-163.

Reis, P.J.; Variations in the S content of wool.; Biology Skin Hair Growth, Proceedings Symposium; 1964, pp. 365-375.

Rogers, G.E.; "Some observations on the proteins of the inner root sheath cells of hair follicles." Biochimica et Biophysica Acta; vol. 29. 1958, pp. 33-43.

Rogers, G.E. ; et al; "Keratin protofilaments and ribosomes from hair follicles."; Nature, vol. 205, 1965, pp. 77-78.

Rogers, G.E. et al.; "An approach to the investigation of protein biosynthesis in hair follicles." Biology of Skin Hair Growth, Proceedings, 1965, pp. 329-343.

Rogers, G.E.; "Genetic engineering for novel fibres."; Journal of the Textile Institute; vol. 91, part 3, Special Issue, 2000, pp. 24-31.

Rogers, G.E.; "Improvement of wool production through genetic engineering."; Trends in biotechnology (Personnal edition); vol. 8, 1990, pp. 6-11, 32 references.

Rogers, G.E.; "Proteins of the inner-root-sheath cells of hair follicles."; Biochimica et Biophysica Acta; vol. 29, 1958, pp. 33-43.

Rogers, G.E.; "Structural and biochemical features of the hair follicles."; Epidermis; 1964, pp. 179-236.

Rogers, G.E.; "Structure and biochemistry of keratin."; The Biological Basis of Medicine.; vol. 6, 1969, pp. 21-57.

Rogers, G.E.; "Synthesis and cross-linking in the structure and growth of hair keratins." Clinics in Dermatology; vol. 6, No. 4, 1988, pp. 26-31.

Rogers, G.E.; et al; "Protein biosynthesis in hair follicles."; Biology of Skin Hair Growth., Proceedings ; 1965, pp. 329-343.

Rogers, G.E.; et al; "A procedure for the culture of hair follicles as functionally intact organoids."; Clinics in Dermatology; vol. 6, No. 4, 1988. pp. 36-41.

Rogers, G.E.; et al; "A sensitive assay for the enzyme activity in hair follicles and epidermis that catalyzes the peptidyl-arginine-citrulline posttranslational modification." Current Problems Dermatology; vol. 11, 1983, pp. 171-184.

Rogers, G.E.; et al; "Organization and expresson of hair follicle genes."; Journal of Investigative Dermatalogy; vol. 101, 1993, pp. 50 S-55 S.

Rogers, G.E.; et al; "Themes in the molecular structure of hair—discussion." Annals New York Academy Science; vol. 642, 1991, pp. 100-106.

Roop, D.R.; Cheng, C.K.; Titterington, L.; Meyers, C.A.; Stanley, J.R.; Steinert, P.M.; Yuspa, S.H.; "Synthetic peptides corresponding to keratin subunits elicit highly specific antobodies." The Journal of Biological Chemistry; vol. 259, No. 13 1984, pp. 8037-8040.

Ross, S.A.; et al; "Nickel complexes of cysteine- and cystine-containing peptides: Spontaneous formation of disulfide-bridged dimers at neutral pH."; Inorganic Chemistry, vol. 37 (20), 1998, pp. 5358-5363.

Rouse, J.G.; et al; "A review of keratin-based biomaterials for biomedical applications." Materials; vol. 3, 2010, pp. 999-1014.

Rowlands, R.J.; "Periodicity in high-sulphur proteins from wool."; Nature; vol. 246, No. 5434, 1973, pp. 530-531.

Sadova, S. F.; et al; "Grafting of vinyl monomers onto wool keratin in an oxidation-reduction system."; Zh. Vses. Khim. O-va, vol. 12(5), 1967, pp. 596-597.

Sander, G.; et al; "Expresssion of the homeobox gene, Barx2, in wool follicle development."; Journal of Investigative Dermatology; vol. 115, No. 4, 2000, pp. 753-756.

Sauk, J.J. et al; "Reconstitution of cytokeratin filaments in vitro: Further evidence for the role of nonhelical peptides in filament assembly."; The Journal of Cell Biology; vol. 99, 1984, pp. 1590-1597.

Schaller, J.; et al; "Membranes prepared from keratin-polyacrylonitrile graft copolymers." Journal of Applied Polymer Sciences; vol. 25(5), 1980, pp. 783-794.

Schornig, M.; Heumann, R.; Rohrer, H.; "Synthesis of nerve growth factor mRNA in cultures of developing mouse whisker pad, a peripheral target tissue of sensory trigeminal neurons."; The Journal of Cell Biology; vol. 120, No. 6, Mar. 1993, p. 1471-1479.

Schrooyen, P.M.M.; et al; "Biodegrable films from selectively modified feather keratin dispersions."; Polymer Preprints; vol. 39, No. 2, 1998, pp. 160.

Schrooyen, P.M.M.; et al; "Polymer films from chicken feather keratin."; Book of Abstracts, American Chemical Society National Meeting Boston, 1998.

Shah, M.; et al.; "Neutralisation of TGF-$\beta_1$ and TGF-$\beta_2$ or exogenous addition of TGF-$\beta_3$ to cutaneous rat wounds reduces scarring." Journal of Cell Science; vol. 108, 1995, pp. 985-1002.

Sizin, T.L.; "The occurance of azelaic acid among the oxidation products of keratin." Z. Physiology Chemistry: vol. 62, 1910, pp. 226-228.

Skerrow, D.; Skerrow, C.J.; Hunter, I.; "Epidermal alpha-keratin is neutral-buffer-soluable and forms intermediate filaments under physiological conditions in vitro."; Biochimica et Biophysica Acta; vol. 915. 1987, pp. 125-131.

Smith, A.L.; et al; "Oxidation of Wool—The Effect of Hydrogen Peroxide." Rayon Textile Monthly; vol. 39, 1936. pp. 39,40.

Smith, A.L.; et al; "Oxidation of Wool: The lead acetate test for hydrogen peroxide bleached wool."Journal of Research of the National Bureau of Standards, vol. 16, 1936, pp. 309-312.

Sparrow, L.G.; et al; "Further resolution of the low sulphur S-carboxymethylkerateine fraction from wool by acrylamide-gel electrophoresis."; Journal of Textile Institute; vol. 63, No. 11, 1972, pp. 619-621.

Starger, J.M.; Brown, W.E.; Goldman, A.E.; Goldman, R.D.; "Biochemical and immunological analysis of rapidly purified 10-nm filaments from baby hamster kidney (BHK-21) cells." The Journal of Cell Biology, vol. 78, 1978, pp. 93-109.

Stary, Z.; "Brominated keratin and oxykeratin."; Z. Physiology Chemistry; vol. 144, 1925, pp. 147-177.

Stary, Z.; "Solubility and digestibility of the degradation products of albumoids." Z. Physiology Chemistry; vol. 136, 1924, pp. 160-172.

Steinert, P.M.; et al; "In vitro studies on the synthesis of guinea pig hair keratin proteins." Biochimica et Biophysica Acta; vol. 312, 1973, pp. 403-412.

Stenn, K.S.; "The molecular and structural biology of hair, Introduction."; Annals of New York Academy of Sciences; vol. 83, 1959, pp. 359-512.

Stenn, K.S.; et al.; "Controls of hair Follicle cycling.."; Physiological Reviews; vol. 81, No. 1, 2001, pp. 449-494.

Stenn, K.S.; et al.; "Hair follicle growth controls." Dermatologic Clinics; vol. 14, No. 4, 1996, pp. 543-558.

Stenn, K.S.; et al.; "Molecules of the cycling hair follicle—a tabulated review." Journal of Dermatalogical Science 7(Suppl.) 1994, pp. 109-124.

Stephenson, N.A.; et al; "Preparation and dioxygen binding properties of a new cobalt (II) complex and the crystal structure of the corresponding copper (II) adduct."; Journal of the Chemical Society, Dalton Transactions: Inorganic Chemistry, 150th Anniv. Celebration issue, 1991, pp. 733-738.

Stokes,G.D.; Dunson, W.A.; "Passage of water and electrolytes through natural and artificial keratin membranes." Desalination; vol. 42, 1982, pp. 321-328.

Struessmann, A.; et al.; "Specific radiolabeling of keratin proteins by amidination."; Journal of Chromatography, vol. 268, 1983, pp. 306-310.

Suzuki, E.; et al; "X-ray diffraction and infrared studies of an $\alpha$-helical fragment from $\alpha$-keratin." Journal of Molecular Biology; vol. 73, 1973, pp. 275-278.

Tachibana, A. et al.; "Fabrication of wool keratin sponge scaffolds for long-term cell cultivation." Journal of Biotechnology, vol. 93, 2002 pp. 165-170.

Tanabe, T.; et al.; "Keratins : Prospective proteinous biomaterial." Protein Engineering; vol. 1, 2001, pp. 247-259.

Tanabe, T.; Tachibana, A.; Yamauchi, K.; "Keratins: prospective proteinous biomaterial."; Recent Research Developments in Protein Engineering; vol. 1(Pt.2),2001, pp. 247-259.

Tazawa, T.; et al; "Anti-hair keratin monoclonal antibody (HKN-2)."; The Journal of Dermatology; vol. 12, 1985, pp. 313-317.

Thomas, H.; et al; "Isolation of the microfibrillar proteins of wool in the disulfide form." Melliand Textilberichte; vol. 65, No. 3, 1984, pp. 208-209.

Tsai, A.G.; et al; "High viscocity plasma expanders: Volume restitution fluids for lowering the transfusion trigger."; Biorheology, vol. 38 (2-3), 2001, pp. 229-237.

Tsai, A.G.; et al; "The unusual properties of effective blood substitutes."; Keio Journal of Medicine; vol. 51 (1), 2002, pp. 17-20.

Tsuchida, E.; "Oxygen ligation of macromolecule-porphyrin complexes."; Journal of the Chemical Society of Japan; No. 6, 1988, pp. 845-852.

Tsuchida, E.; et al; "Cobalt (II)/poly(ethyleneimine) membrane with oxygen binding ability."; Makromolekulare Chemie; vol. 3 (10), 1982, pp. 693-696.

Tucker, D.J.; et al; "Variations in goat fiber proteins."; Australian Journal of Agriculture Research vol. 40, No. 3, 1989, pp. 675-683.

Ueyama, N.; et al; "A novel method for determining the chelation ability of the cysteine-containing peptides with 3,4-toluenedithiol. Application to .cents .2Fe-2S-ferredoxin model systems."; Bulletin of the Chemical Society of Japan; vol. 60 (1), 1987, pp. 283-287.

Van Neste, D.; "The growth of human hair in nude mice."; Dermatologic Clinics; vol. 14, No. 4, 1996, pp. 609-617.

Vasak, M.; et al; "Metal thiolate clusters in cobalt (II)-metallothionein."; Proceedings of the National Academy of Sciences of the United States of America; vol. 78 (11), 1981, pp. 6709-6713.

Vogeli, G.; et al; "High-Sulfur Protein Gene Expression in a Transgenic Mouse." Annals New York Academy of Sciences; vol. 642, 1991, pp. 21-30.

Ward, K.A. ; et al.; "The structure of the wool keratin microfibrillar genes." Proceedings of the Australian Biochemical Society; vol. 15, 1983, pp. 70.

Ward, K.A.; "Changes in wool follicle keratinocyte protein-biosynthesis mediated by inhibitors of follicle bulb cell-proliferation."; Proceedings of the Australian Biochemical Society; vol. 9, 1976, pp. 57.

Ward, K.A.; "Study of keratin biosynthesis in isolated wool follicle cells." Proceedings of the Australian Biochemical Society; vol. 7, 1974, pp. 93.

Ward, K.A.; et al; "Change in wool follicle keratinocyte protein-biosynthesis mediated by inhibitors of follicle bulb cell proliferation."; Proceedings of the Australian Biochemical Society; vol. 9, 1976, pp. 57.

Weber, K.; Geisler, N.; "The structural relation between intermediate filament proteins in living cells and the alpha-keratins of sheep wool" The EMBO Jjournal; vol. 1 No. 10, 1982, pp. 1155-1160.

Weiss, R.A.; Guilett, Y.A,G.; Freedberg, I.M.; Farmer, E.R.; Small, E.A.; Weiss, M.M.; Sun, T.T; "The use of monoclonal antibody to keratin in human epidermal disease: Alterations in immunohistochemical staining pattern." vol. 81, No. 3, 1983, pp. 224-230.

Werner, S.; et al.; "Large induction of keratinocyte growth factor expression in the dermis during wound healing." Proceedings of the National Academy of Sciences, USA; vol. 89, 1992, pp. 6896-6900.

Whitbread, L.A.; et al; "Expression of the intermediate filament gene, K15, in the basal cell layers of epithelia and the hair follicle."; Experimental Cell Research; vol. 244, 1998, pp. 448-459.

Widra, A.; "Ascoporogenesis by nannizzia grubyia on a soluble fraction of keratin." Mycopathologia et Mycologia Applicata; vol. 30, No. 2, 1966 pp. 141-144.

Wilson, B. W.; et al.; "Complete sequence of a type-I microfibrillar wool keratin gene."; Gene; vol. 73, No. 1, 1988, pp. 21-31.

Wilson, N.; et al; "The role of BMP-2 and BMP-4 in follicle initiation and the murine hair cycle."; Experimental Dermatology; vol. 8, No. 4, 1999, pp. 367-368.

Wolski, T.; Szumilo, H.; "Studies on the kinetics of dissolving feather keratin in the water-urea system." Acta Alimentaria Polinica; vol. 8, (32) No. 1-2, 1982, pp. 102-108.

Wormell, R. L.; "Regenerated fibers from wool." Brit. Rayon Silk Journal; vol. 26, No. 309, pp. 55.

Wormell, R.L.; "Regenerated protein fibres from wool and casein"; The Journal of the Textile Institute; vol. 39, 1948, T219-T224.

Wormell, R.L.; "Wool, silk and regenerated protein fibers-chemistry." Rev. Textile Progress; vol. 9, 1957, pp. 51-62.

Wortmann, F.J.; et al.; "A method for isolating the cortex of keratin fibers."; Textile Research Journal; vol. 52, 1982, pp. 479-481.

Yakubovich, T.N.; Teslenko, V.V.; Zub, Y.L; "Carriers of molecular oxygen on the basis of metal complexes incorporated in polyorganosiloxane matrices."; Journal of Inorganic and Organometallic Polymers; vol. 6, No. 1, 1996, pp. 43-49.

Yamamura, T.; et al; "Confirmation control of peptides by metal ions. Coordination confirmation correlation observed in a model for Cys-X-Y-Cys/M2+ in proteins."; Inorganic Chemistry; vol. 36 (21), 1997, pp. 4849-4859.

Yamauchi, K. et al.; "Novel proteinous microcapsules from wool keratins." Colloids and Sudaces, B: Biointertaces; vol. 9, 1997, pp. 117-119.

Yamauchi, K.; "Dissolution of hair and wool. Keratin polymers." Kobunshi Kako; vol. 4i, No. 1, 1994, pp. 14-19.

Yamauchi, K.; "Perspective in chemistry and applications of keratins." Kobunshi; vol. 50, No. 4, 2001, pp. 240-243.

Yamauchi, K.; "Polymer films fom keratin."; Fragrance Journal; vol. 21 (5), 1993, pp. 62-67.

Yamauchi, K.; "Preparation of stable aqueous solution of keratins, and physicochemical and biochemical properties of films." Polymer Preprints—American Chemical Society, Division of Polymer Chemistry; vol. 39, No. 1, pp. 357-358.

Yamauchi, K.; et al.; "Cultivation of Mouse L929 Fibroblast Cells on Keratins."; Kobunshi Gakkai Yokoshu (Polymer Preprints), Japan; vol. 44, No. 3,1995, pp. 503.

Yamauchi, K.; et al.; "Preparation of stable aqueous solution of keratins, and physicochemical and biodegradational properties of films." Journal of Biomedical Materials Research; vol. 31, No. 4, 1996, pp. 439-444.

Yamauchi, K.; et al; "Enhanced cell adhesion on RGDS-carrying keratin film."; Material Science & Engineering, C.: Biomimetic and Supermolecular Systems; vol. C23, No. 4, 2003, pp. 467-472.

Yao, X.; et al; "Oxygen carrying porphyrin-protein complexes the effect of iron (II) prophyrin structure on dioxygen binding performance."; Research Communications in Biochemistry and Cell & Molecular Biology; vol. 5 (1&2) 2001, pp. 171-174.

Yoshimizu, H.; et al; "C CP/MAS NMR study of the conformation of stretched or heated low-sulfur keratin protein films." Macromolecules,; vol. 24, 1991, pp. 862-866.

Zackroff, R.V.; Goldman, R.D.; "In vitro assembly of intermediate filaments from baby hamster kidney (BHK-21) cells." Proceedings of the National Academy of Sciences, USA; vol. 76, No. 12, pp. 6226-6230.

Zahn, H. et al.; "Reactivity of amino acid side chains. 18. Reactions of p-fluoro-m,m'-dinitrodiphenyl sulfone and p,p'-difluoro-m,m'-dinotrodiphenyl sulfone with wool keratin and silk fibroin."; Kolloid Zeitschrift fuer Polymere; vol. 5, 1973 pp. 289-298.

Zahn, H. et al.; "Wool as a biological composite structure."; Industrial & Engineering Chemistry Product Research and Development; vol. 19, 1980, pp. 496-501.

Zahn, H.; "Progress report on hair keratin research."; International Journal of Cosmetic Science; vol. 24, 2002, pp. 163-169.

Zahn, H.; "Structure and chemistry of wool fibers." Kolloid-Z; vol. 100, 1942, pp. 283-298.

Zahn, H.; "The role of mohair keratin research." Melliand Textilberichte; vol. 71, 1991, pp. 926-931.

Zahn, H.; "Wool research taking part in comtemporary chemistry and physics." Arbeitsgemeinschaft Forsch. Landes Nordheim-Westfalen; vol. 75, 1957, pp. 47-80.

Zahn, H.G.; et al; "2-Dimensional keratin patterns of human hair including cosmetically treated ones."; Journal of Forensic Science Society; vol. 24, No. 4, 1984, pp. 432.

Zahn,H. et al.; "Wool as a biological compounding material." Schriftenreihe des Deautschen Wollforschungsintitutes; vol. 76, 1978, pp. 18-25.

Alexander, P.; Earland, C.; "Structure of wool fibers—Isolation of an α and β-protein in wool." Nature; vol. 166, 1950.

Almog, J.; Baldwin, J.E.; Dyer, R.L.; Duff, J.; Wilkerson, C.J.; "Reversible binding of dioxygen to mesoporphyrin IX derivatives at low temperatures." Journal of the American Chemical Society; (96:17) 1974, pp. 5600-5601.

Almog, J.; et al; "Reversible binding of dioxygen to mesoporphyrin IX derivatives at low temperatures."; Journal of the American Chemical Society; vol. 96(17), 1974, pp. 5600-5501.

Almog, J.; et al; "Reversible oxygenation and autoxidation of a capped porphyrin iron (II) complex."; Journal of the American Chemical Society; vol. 97(1), 1975, pp. 227-228.

Amiya, T.; et al; "Conformational studies of the α-helical proteins from wool keratins by c.d." International Journal of Biological Macromolecules; vol. 4, 1982, pp. 165-172.

Ando, H. ; et al; "Separation and characterization of keratin components of merino wool. III: Removal of cuticle by ultrasonic irradiation." Bulletin of the Institute for Chemical Research, Kyoto University; vol. 31, No. 3, 1975, pp. 81-85.

Ashkenasy, G.; et al; "Assemblies of "hinged" iron-porphyrins as potential oxygen sensors."; Journal of the American Chemical Society; vol. 122, No. 6, 2000, pp. 1116-1122.

Baldwin, J.E.; et al; "Binding of dioxygen to iron (II), Reversible behavior in solution."; Journal of the American Chemical Society; vol. 95 (17), 1973, pp. 5757-5759.

Barr, M.; "Oxidation, reduction and hydroysis of wool keratin."; Iowa State Coll. Journal of Science, vol. 12, 1937, pp. 106-107.

Bawden, C.S.; et al; "Expression of bacterial cysteine biosynthesis genes in transgenic mice and sheep: toward a new in vivo acid biosynthesis pathway and improved wool growth." Transgenic Research; vol. 4,1995, pp. 87-104.

Bawden, C.S.; et al; "Expression of wool intermediate filament keratin transgene in sheep fibre alters structure."; Transgenic Research; vol. 7, 1998, pp. 273-287.

Bawden, C.S.; et al; "Improvement of wool quality by transgenesis."; Science Update, Conf: OECD, 2001, pp. 67-76.

Bawden, C.S.; et al; "Sheep transgenesis with keratin and non-keratin genes: expression in the wool follicle for the modified fibre properties and growth rates."; Experimental Dermatology; vol. 8, 1999, pp. 342-343.

Berse, B.; et al.; "Vascular permeability factor (Vascular endothelial growth factor) gene is expressed differentially in normal tissues, macrophages, and tumors." Molecular Biology of the Cell; vol. 3, 1992, pp. 211-220.

Besse, D.; et al; "Synthesis of selenocysteine peptides and their oxidation to diselenide-bridged compounds."; Journal of Peptide Science; vol. 3 (6), 1997, pp. 442-453.

Bettex-Galland, M. et al.; "Advances in Protein Chemistry." Academic Press, vol. 20, 1965.

Bhatanagar, G.M.; et al; "The confirmation of the high-sulphur proteins of wool. The preparation and properties of water-soluble metakeratin." International Journal of Protein Research I; 1969, pp. 199-212.

Bhatnagar, G.M. et al; "Difference sprectra of kerateine-B."; International Journal of Protein Research; vol. 1 No. 3, 1969, pp. 213-219.

Bhatnagar, G.M.; et al; "Assessment of confirmational changes in low-sulfur S-(carboxymethyl)keratin from wool."; Australian Journal of Biological Sciences; vol. 20, No. 4, 1967, pp. 827-836.

Bhatnagar, G.M.; et al; "The conformation of the high sulphur proteins of wool. I The preparation and properties of a water soluble metakeratin."; International Journal of Protein Research; vol. 1 (3), 1969, pp. 199-212.

Bhatnagar, G.M.; et al; "The conformation of the high-sulphur proteins of wool. II—Difference spectra of kerateine-B." International Journal of Protein Research I; 1969, pp. 213-219.

Blagrove, R.J.; Frenkel, M.J.; Gillespie, J.M.; "The electrophoresis of the high-tyrosine proteins of keratins on cellulose acetate strips."; Comparative Biochemistry Physiologoly; vol. 50B, 1975, pp. 571-572.

Blessing, M.; et al.; "Transgenic mice as a model to study the role of TGF-β-related molecules in hair follicles." Genes and Development; vol. 7, 1993, pp. 204-215.

Bradbury, J.H.; "Structure and chemistry of keratin fibers."; Advances in Protein Chemistry; vol. 27, 1973, pp. 111-211.

Bradbury, J.H.; "The structure and chemistry of keratin fibers." Advanced Protein Chemistry; vol. 27, 1973, pp. 111-211.

Bradbury, J.H.; et al.; "Advances in Protein Chemistry." vol. 27, 1973, pp. 222-375.

Bradbury, J.H.; et al; "Observations by light and electron microscopy on wool cuticle fractions obtained by ultrasonics."; Textile Research Journal; vol. 33, No. 4, 1963, pp. 251-257.

Bradbury, J.H.; et al; "Separation of chemically unmodified histiological components of keratin fibers and analyses of cuticles."; Nature; vol. 210, No. 5043, 1966, pp. 1333-1334.
Breinl, F.; et al; "The oxidative breaking up of keratin through treatment with hydrogen peroxide." Z.Physiol. Chemistry; vol. 52, 1907, pp. 158-169.
Broad, A.; Gillespie, J.M., Reis, P.J.; "The influence of sulphur-containing amino acids on the biosynthesis of high-sulphur wool proteins." Australian Journal of Biological Sciences; vol. 23, 1970, pp. 149-164.
Brown, L.F.; et al.; "Expression of vascular permeability factor (Vascular Endothelial Growth Factor) by epidermal keratinocytes during wound healing."; Journal of Experimental Medicine; vol. 176, 1992, pp. 1375-1379.
Brunner, H.; Brunner, A.; "Fractionation of tyrosine-rich proteins from oxidized wool by ion-exchange chromatography and preparative electrophoresis."; European Journal Biochemistry; vol. 32, 1973, pp. 350-355.
Bryson, W.G.; et al; "The analytical tools of proteomics provide new insights into the expression of the wool genome, keratin chemistry and textile processing."; Wool Tcehnology and Sheep Breeding; vol. 49, No. 4, 2001, pp. 246-260.
Cameron, J.H.; et al; "Nickel (II) and cobalt (II) complexes of potentially quinquedentate macrobicyclic ligands. Reversible binding to dioxygen to a cobalt (II) complex."; Journal of the Chemical Society, Dalton Transactions: Inorganic Chemistry; vol. 3, 1993, pp. 397-402.
Campbell, M.E.; Whiteley, K.J.; Gillespie, J.M.; "Compositional studies of high and low-crimp wools."; Australian Journal of Biological Sciences; vol. 25, 1972, pp. 977-987.
Carey, J.R.; et al; "Design and synthesis of novel metalloproteins through reversible encapsulation of metal complexes by proteins." Abstract of Papers, 222nd ACS National Meeting, 2001.
Chatani, E.; et al; "A film formation technology of wool keratin."; Textile and Fashion; vol. 14(5), 1997, pp. 227-235.
Gillespie, J.M.; "Reaction of Sodium Borohydride with wool." Nature; vol. 183 No. 4657, 1959, pp. 322, 323.
Gillespie, J.M.; Inglis, A.S.; "High-sulphur proteins as a major cause of variation in sulphur content between α-keratins." Nature; vol. 207, 1965, pp. 1293,1294.
Gillespie, J.M.; Marshall, R.C.; "A comparision of the proteins of normal and trichothiodystrophic human hair." The Journal of Investigative Dermatology; vol. 80, 1983, pp. 195-202.
Gillespie, J.M.; Marshall, R.C.; Moore, G.P.; Panaretto, B.A.; Robertson, D.M.; "Changes in the proteins of wool following treatment of sheep with epidermal growth factor."; The Journal of Investigative Dermatology; vol. 79, No. 3, 1982, pp. 197-200.
Gillespie, J.M.; Reis, P.J.; "The dietary regulated biosynthesis of high-sulphur wool proteins."; Biochemistry Journal; vol. 98, 1966, pp. 669-677.
Gillespie, J.M.; Simmonds, D.H.; "Amino acid composition of a sulphur-rich protein from wool."; Biochimica et Biophysica Acta; vol. 39, 1960, pp. 538-539.
Gillespie, M.J. et al.; "Variable composition of hair and high-sulfur proteins in trichothiodystrophy." *Journal of Applied Cosmetology*; vol. 7, No. 2, 1989, pp. 39-48.
Gillespie, M.J.; "Keratin structure and changes with copper deficiency."; Australian Journal of Dermatology; vol. 14, No. 3, 1973, pp. 127-131.
Gillespie, M.J.; "Swelling of keratins in formic acid." Textile Research Journal; vol. 40, No. 9, 1970, pp. 853-855.
Gillespie, M.J.; "The relation between the crimp of wool and its content of high-sulfur proteins."; Textile Research Journal; vol. 35, No. 12, 1965, pp. 1128-1129.
Gillespie, M.J.; et al; Evidence of homology in a high-sulfur protein fraction (SCMK-B2) of wool and hair α-keratins; Biochemistry Journal; vol. 110, No. 2, 1968, pp. 193-200.
Gillespie,J.M.; "Proteins rich in glycine and tyrosine from keratins."; Comparative Biochemistry and Physiology; vol. 41B, 1972, pp. 723-734.
Gillis, J.N.; et al; "Selective retention of oxygen using chromatographic columns containing metal chelate polymers."; Analytical Chemistry; vol. 57(8), 1985, pp. 1572-1577.

Goddard, D.R. et al; "A Study on Keratin."; Journal of Biological Chemistry; vol. 106, 1934, pp. 605-614.
Gough, K.H. et al; "Amino acid sequences of alpha-helical segments from S-carboxymethylkerateine-A. Complete sequence of a type-I segment."; Biochemical Journal; vol. 173 (2), 1978, pp. 373-385.
Green, M.R.; Basketter, D.A.; Couchman, J.R.; Rees, D.A.; "Distribution and number of epidermal growth factor receptors in skin is related to epithelial cell growth.;"Developmental Biology; vol. 100, 1983, pp. 506-512.
Greven, R.; et al.; "Morphological origin of the S-carboxymethyl kerateines of wool."; Textile Research Journal vol. 56; 1986, pp. 523-526.
Grotendorst, G.R.; et al.; "Novel transforming growth factor β response element controls the expression of the connective tissue growth factor gene."; Cell Growth and Differentiation; vol. 7, 1996, pp. 469-480.
Han, C.H.; et al; "Effect of glycerol addition on the structure and properties of soluble wool keratose films."; Journal of the Korean Fiber Society; vol. 37,No. 8, 2000, pp. 442-447.
Hanukoglu, I.; et al.; "The cDNA sequence of a human epidermal keratin: Divergence of the sequence but conservation of structure among intermediate filament proteins." Cell; vol. 31, 1982, pp. 243-252.
Happey, F.; "Polycrystralline structure of wool." Nature; No. 4218, 1950, pp. 397-398.
Happey, F.; Wormell, R. L.; "Regenerated keratin fibers from wool." Journal Textile Inst.; vol. 40, 1949, pp. T855-T869.
Happey, F.; Wormell, R. L.; "Regenerated keratin fibers."; Nature ; vol. 163, 1949, p. 18.
Harding, H.W.J.; et al; "Enzymic conversion of arginine to citrulline in a hair protein precursor."; Proceedings of the Australian Biochemical Society; ; vol. 9, 1976, pp. 18.
Harding, H.W.J.; Rogers, G.E.; "Formation of ε (γ-Glutamyl) lysine cross-link in hair proteins. Investigation of transamidases in hair follicles." The Journal of Biochemistry; vol. 11, No. 15, 1972 pp. 2858-2863.
Hardy, M.H.; "The Secret life of the hair follicle."; Trends in Genetics; vol. 8, No. 2, 1992, pp. 55-60.
Harrap, B.S.; et al; "Soluble derivatives of feather keratin. (I) Isolation, fractionation and amiino acid composition." Biochemistry Journal; vol. 92, 1964, pp. 8-18.
Harris, M.; et al.; "Testing for oxidation damage of wool by alkali solubility." The Textile Manufacturer; vol. 63, 1937, pp. 36,37.
Hewish, D.R.; et al; "In vitro growth and differentiation of epithelial cells derived from post-embryonic hair follicles."; Australian Journal of Biological Sciences; vol. 35, No. 1, 1982, pp. 103-109.
Hiroshi, S.; et al; "Differential Thermal Analysis of component proteins from wool." Institute for Chemical Research, Kyoto University, Uji, Kyoto; vol. 38, 1982, pp. 517-522.
Hogg, D.M.; et al; "Amino acid sequences of alpha-helical segments from S-carboxymethylkerateine-A. Tryptic and chymotryptic peptides from a type II segment"; Biochemical Journal; vol. 173(2), 1978, pp. 353-363.
Horn, J.C.; Speakman, P.T.; "Relative molecular masses of reduced wool keratin polypeptides" Biochemistry Society Transcript, vol. 14, 1986, pp. 333, 334.
Hu, J.; et al; "Preparation of stable solution of keratin from human hair and structure and properties of the cast film."; Gaofenzi Cailiao Kexue Yu Gongcheng; vol. 18 (2), 2002, pp. 131-133.
Humphries, M.; "Protein-silicone copolymers."; Cosmetics News; vol. 16, No. 92, 1993, pp. 313-318.
Hynd, P.I.; et al; "Amino acid transport in wool and hair follicles."; Experimental Dermatology; vol. 8, 1999, pp. 325-356.
Hübner, G.; et al.; "Strong induction of activin expression after injury suggests an important role of activin in wound repair."; Developmental Biology; vol. 173, 1996, pp. 490-498.
Igarashi, A.; et al.; "Regulation of connective tissue growth factor gene expression in human skin fibroblasts and during wound repair." Molecular Biology of the Cell; vol. 4, 1993, pp. 637-645.
Ikkai, F.; et al; "Dynamic light scattering and circular dichroism studies on heat-induced gelation of hard-keratin protein aqueous solutions."; Biomacromolecules, vol. 3, No. 3, 2002, pp. 482-487.

Ito, H.; et al; "Biocompatability of denatured keratins from wool."; Kobunshi Ronbunshu; vol. 39(4), 1982, pp. 249-256.

Iwatsuki, K.; Viac, J.; Reano, A; Morera, A; Staquet, M.J.; Thivolet, J.; Monier, J.C.; "Comparative studies on the naturally ocurring antikeratin antibodies in human sera."; The Journal of Investigative Dermatology; vol. 87, No. 2, 1986, pp. 179-184.

Jahoda, C.A.B.; et al.; "Dermal-Epidermal Interactions: Adult Follicle-derived cell populations and hair growth."; Dermatologic Clinics; vol. 14, No. 4 1996, pp. 573-583.

Jenkins, B.J. ; et al; "Isolation and characterization of a sheep cysteine-rich cuticle keratin pseudogene."; DNA Sequence; vol. 3, 1992, pp. 181-184.

Jenkins, B.J. et al; "Differential expression of genes encoding a cysteine-rich keratin in the hair cuticle."; Journal of Investigative Dermatology; vol. 103, 1994, pp. 310-317.

Jenkins, B.J.; et al; "Differential expression of genes encoding a cysteine-rich keratin family in the hair cuticle."; Journal of Investigative Dermatology; vol. 103, No. 3, 1994, pp. 310-317.

Jezowska-Trezebiatowska, B.; et al; "New cobalt (II) complexes, reversibly binding oxygen in aqueous solution."; Bulletin de l'Academie Polonaise des Sciences, Serie des Sciences Chimiques; vol. 20 (3), 1972, pp. 187-192.

Johnson, P.C.; et al; "Oxidative metabolism and blood flow regulation: The search for the missing link."; Journal of Vascular Research; vol. 37 (1) 2000, pp. 83.

Jones, C.M.; et al.; "Involvement of Bone Morphogenetic Protein-4 (BMP-4) and Vgr-1 in morphogenesis and neurogenesis in the mouse."; Development; vol. 111, 1991, pp. 531-542.

Jones, L.N.; "Studies on Microfibrils from alpha-Keratin."; Biochimica et Biophysica Acta ; vol. 446. 1976, pp. 515-524.

Jones, L.N.; et al; "Studies of developing human hair shaft cells in vitro."; Journal of Investigative Dermatology; vol. 90, No. 1, 1988, pp. 58-64.

Jozefowicz, M.; Jozefonvicz, J; "Functional Polymers and Cells"; Biomaterials; vol. 16, No. 4, 1988, pp. 831-870.

Katoh, K.; et al; "Multi-functionalization of fiber made of natural polymer."; Aichi-ken Sangayo Gijutsu Kenkyusho Kenkyu Hokoku; vol. 1, 2002, pp. 174-177.

Katsuumi, K.; Ito, M; Kazama, T.; Sato, Y.; "Two dimensional electrophoretic analysis of human hair keratins, especially hair matrix proteins." Archives of Dermatological Research; vol. 281, 1989, pp. 495-501.

Kawano, Y.; et al; "Film and gel of keratins."; Kagaku to Seibutsu; vol. 13 (5), 1975, pp. 291-292.

Kemp, D.J. et al; "Differentiation of avian keratinocytes. Characterization and relationships of the keratin proteins of adult and embryonic feathers and scales."; Biochemistry; vol. 11, No. 6, 1972, pp. 969-975.

Kemp, D.J.; Rodgers, G.E.; "Immunological and immunofluorescent studies on keratin of the hair follicle."; Journal of Cell Science; vol. 7, 1970, pp. 273-283.

Kikkawa, M.; et al; "Solubilization of keratin. Solubilization of feather keratin by oxidation with performic acid."; Hikaku Kagaku,(Leather Chemistry) vol. 20(3), 1974, pp. 151-162.

Klement, V.; et al; "The use of computer-analysis for the quantification of 2-D electrophoretic hair keratin patterns—a pilot study."; Journal of the Forensic Science Society; vol. 24, No. 4, 1984, pp. 440.

Koga, J. et al.; "FTIR study on structural transformation of keratin films induced by stretching."; Journal of Applied polymer Science; vol. 37, 1989, pp. 2131-2140.

Kothapalli, D.; et al.; "Transforming growth factor β induces anchorage-independent growth of NRK fibroblast via a connective tissue growth factor-dependent signaling pathway." Cell Growth and Differentiation; vol. 8, 1997, pp. 61-68.

Kowalska, K.; et al; "New bacterial peptides isolated from structural proteins (keratin of porcine bristle)."; Peptides; Proceedings of the European Peptide Symposium, 25th, 1998, pp. 792-793.

Kozlowski, H.; et al; "Nickel (II) complexes with sulfhydryl containing pepetides. Potentiometric and spectroscopic studies."; Journal of Inorganic Biochemistry; vol. 29 (3), 1987, pp. 187-197.

Kuczek, E.S.; et al; "Sheep wool (glycine+tyrosine)-rich keratin genes: a family of low sequence homology."; European Journal of Biochemistry; vol. 166, 1987, pp. 79-85.

Kulkarni, V.G.; "Further studies on the microfibrils from wool keratin. Part I: the isolation of microfibrils."; Textile Research Journal; vol. 46, No. 11, 1976, pp. 833-835.

Kurimoto, A.; et al.; "Conjugation of keratin sponge with bioactive substances utilizing free cysteine residues. Conjugation of lysozyme."; Nippon Kagakkai Koen Yokoshu; vol. 7, No. 2, 2001, pp. 818.

Kvedar, J.C.; et al.; "Cytokeratins of the bovine hoof : classification and studies on expression."; Biochimica et Biophysica Acta; vol. 884, 1986, pp. 462-473.

Lambre, C.R.; Alaoui-Slimani, N.; Bignon, J.; "An enzyme immunoassay for the auto-antibodies to keratin in normal human serum and in pleural fluids from patients with various malignant or non-malignant lung diseases."; Journal of Clinical and Laboratory Immunology; vol. 20, 1986, pp. 171-176.

Laplaza, C.E,; et al; "Helix-loop-helix-peptide as scaffolds for the construction of bridged metal assemblies in proteins: The spectroscopic A—cluster structure in carbon monoxide dehydrogenase."; Journal of the American Chemical Society, vol. 123, (42), 2001, pp. 10255-10264.

Lee, K.Y.; "Characterization of Silk Fibroin/S-carboxymethyl kerateine surfaces: Evaluation of the biocompatibility by contact angle measurement."; Fibers and Polymers; vol. 2, No. 2, 2001, pp. 71-74.

Leeder, J.D.; et al; "Readily extracted proteins from Merino wool."; Textile Research Journal; vol. 52, No. 4, 1982, pp. 245-249.

Lennox, F.G.; "Protein fibers. Chemistry."; Review of Textile Progress Journal; vol. 17, 1967, pp. 81-97.

Lennox, F.G.; et al.; "Photochemical degradation of keratins."; Photochemistry and Photobiology; vol. 9, No. 4, 1969, pp. 359-367.

Leon, N.H.; "The chemical reactivity and modification of keratin fibres." Textile Progress vol. 7, No. 1975, pp. 1-81.

Letter,J.E.; Jordan,R.B.; "Complexing of Nickel(II) by cysteine, tyrosine and related ligands and evidence for zwitterion reactivity." Journal of the American Chemical Society; vol. 9, No. 97, 1975, pp. 2381-2390.

Ley, K.; et al; "Release of cuticle from wool by agitation in solutions of detergents."; Australian Journal of Biological Sciences; vol. 41, No. 2, 1988, pp. 163-176.

Ley, K.F.; et al; "Wool cuticle—new approaches to its production and protein characterization."; Proceedings of the Australian Biochemical Society; vol. 14, 1981, pp. 14.

Li, C-X.; et al; "Purification of natural antikeratin autoantibodies from natural human serum and their effect on human keratinocytes cultured in vivo."; British Journal of Dermatology; vol. 145, No. 5, 2001, pp. 737-748.

Lindley, H. et al.; "High-sulfur protein fractions of keratins."; *Applied Polymers Symposium*; vol. 18, No. 1, 1971, pp. 21-35.

Lindley, H. et al; "Disulphide interchange reactions involving cyclocystine and their relevance to problems of α-keratin structure."; Biochemistry Journal; vol. 108, No. 4, 1968, pp. 701-703.

Lindley, H.; Elleman, T.C.; "The preparation and properties of a group of proteins from the high-sulphur fraction of wool." Biochemistry Journal, vol. 128, 1972, pp. 859-867.

Lindley, H.; et al; "The reactivity of the disulphide bonds of wool." Biochemistry Journal; vol. 139, 1974, pp. 515-523.

Lindley, H.; et al; "The occurance of the Cys-Cys sequence in keratins."; Journal of Molecular Biology; vol. 30, No. 1, 1967, pp. 63-67.

Chatani, E.; et al; "Research on merchandizing technology of wool keratin. Film formation technology of wool keratin."; Owari Textile Research Annual Report No. 93, 1998, pp. 93-101.

Clark, R.A.F. Editor; "The Molecular and Cellular Biology of Wound Repair."; Plenum Press 2nd Edition, 1996, 1988.

Crewther, W.G. et al; "Helix-rich fraction from the low-sulphur proteins of wool."; Nature; vol. 207,(4994), 1965, pp. 295.

Crewther, W.G.; Effect of aftertreatment on the stability of set wool fibers. Comments; Journal of the Society of Dyers and Colourist; vol. 86, No. 5, 1970, pp. 208.

Crewther, W.G.; "The concept of internal pH in wool fibers and the interpretation of data relating to setting."; Journal of the Society of Dyers and Colourist; vol. 81, (4), 1965, pp. 156-158.

Crewther, W.G.; "The viscoelasticity of alpha keratin fibers."; Experimental Dermatology; vol. 8 (4), 1999, pp. 343-344.

Crewther, W.G.; "Preparation and properties of large peptides from the helical regiones of the low-sulfur proteins of wool."; Applied Polymer Symposia; vol. 18, No. 1, 1971, pp. 1-20.

Crewther, W.G.; "Structure of .alpha-keratin."; Textile Research Journal; vol. 42, No. 4, 1972, pp. 251-252.

Crewther, W.G.; "The stress-strain characteristics of animal fibers after reduction and alkylation."; Textile Research Journal; vol. 35, No. 10, 1965, pp. 867-877.

Crewther, W.G.; "Thiol-disulfide interchange reactions in the setting of single wool fibers." Journal of the Society of Dyers and Colourist; vol. 82, No. 1, 1966, pp. 54-58.

Crewther, W.G.; et al; "Effect of S-carboxymethylation of wool proteins on the iodination of tyrosine residues."; Textile Research Journal; vol. 41, No. 3, 1971, 99.267.

Crewther, W.G.; Dowling, L.M.; "The relation between the disulphide content of wool and the two-stage supercontraction of wool fibers in solution of LiBr."; Biochimica et Biophysica Acta; vol. 46, 1961, pp. 605-606.

Crewther, W.G.; et al; "Amino acid sequences of alpha-helical segments from S-carboxymethylkerateine-A. Complete sequence of a type II segment."; Biochemical Journal; vol. 173 (2), 1978, pp. 365-371.

Crewther, W.G.; et al; "Amino acid sequences of $\alpha$-helical segments from S-carboxymethlykerateine-A. Tryptic and chymotryptic peptides from a type-II segment."; Biochemistry Journal; vol. 173, 1978 pp. 353-363.

Crewther, W.G.; et al; "Formation of various crosslinkages in wool and their effect on the supercontraction properties of the fibers."; Textile Research Journal; vol. 37, No. 9, 1967, pp. 736-745.

Crewther, W.G.; et al; "Low-sulfur proteins from $\alpha$-keratins. Inter-relationship between their amino acid compositions, $\alpha$-helix contents, and the supercontraction of the parent keratin." Biopolymers, vol. 4, 1966, pp. 905-916.

Crewther, W.G.; et al; "Reduction of S-carboxymethlycysteine and methionine with sodium in liquid ammonia." Biochimica et Biophysica Acta; vol. 164, 1969, pp. 606-609.

Crewther, W.G.; et al; "Structure of intermediate filaments."; International Journal of Biological Macrmolecules; vol. 5, No. 5, 1983, pp. 267-274.

Crewther, W.G.; et al; "The chemistry of keratins."; Advance Protein Chemistry; vol. 20, 1965 pp. 191-346.

Crewther, W.G.; et al; "The preparation and properties of a helix-rich fraction obtained by partial proteolysis of low sulfur S-Carboxymethylkerateine fromn wool." The Journal of Biological Chemistry; vol. 242, No. 19, 1967, pp. 4310-4319.

Dale, H.N.; "Keratin and other coatings for pills."; Pharmacology Journal; vol. 129, 1932, pp. 494-495.

Damaglou, A.P.; et al; "The hydrolysis by thermolysin of dipeptide derivatives that contain substituted cysteine" Biochemical Journal; vol. 123, No. 3, 1971, pp. 379-384.

Darskus, R.L.; et al.; "Breed and species differences in the hair proteins of four genera of caprini." Australian Journal of Biological Sciences; vol. 24, 1971, pp. 515-524.

Darskus, R.L.; et al; "The possibility of common amino acid sequences in high sulphur protein fractions from wool." Australian Journal of Biological Sciences; vol. 22, 1969, pp. 1197-1204.

De Sanctis, G.; et al; "Mini-myoglobin—Electron paramagnetic resonance and reversible oxygenation of the cobalt derivative."; Journal of Molecular Biology; vol. 222, 1991, pp. 637-643.

Dedeurwaerder, R.A.; et al; "Selective extraction of protein fraction from wool keratin." Nature vol. 203, 1964, pp. 48,49.

Dobb, M.G.; et al; "Electron microscopy of fibrous keratins."; Symposuim of fibrous protein, Int Conf.; 1967, pp. 267-278.

Dowling, L.M.; Crewther, W.G.; Inglis, A.S.; "The primary structure of component 8c-1, a subunit protein of intermediate filaments in wool keratin."; Biochemistry Journal vol. 236, 1986, pp. 695-703.

Dowling, L.M.; Crewther, W.G.; Parry, D.A.D.; "The secondary structure of component 8c-1, of alpha-keratin."; Biochemistry Journal; vol. 236, 1986, pp. 705-712.

Dowling, L.M.; et al; "Effect of the solvent on the iodanation of a tyrosine derivative and its relation to iodination of wool."; Textile Research Journal; vol. 41, No. 1, 1971, pp. 65-69.

Dowling, L.M.; et al; "Isolation of components from the low sulphur proteins of wool by fractional precipitation."; Preparative Biochemistry, vol. 4(3), 1974, pp. 203-226.

Downes, A.M.; et al; "Evaluation of modified [35S] methionine and [35S] casein preparations as supplements for sheep"; British Journal of Nutrition; vol. 24, No. 4, 1970, pp. 1083-1089.

Downes, A.M.; et al; "Matabolic fate of parenterally administered sulphur containing amino acids in sheep and the effects on growth and composition of wool" ; Australian Journal of Biological Sciences; vol. 23, No. 5, 1970, pp. 1077-1088.

Downes, A.M.; Ferguson,K.A.; Gillespie, J.M.; Harrap, B.S.; "A study of the proteins of the wool follicle." Australian Journal of Biological Science; vol. 19. 1966, pp. 319-333.

Dunn, S.M.; et al; "Regulation of hair gene expression."; Experimental Dermatology, vol. 8, 1999, pp. 341-342.

Earland, C.; et al; "Structure of keratin. II. Amino acid content of fractions isolated from oxidized wool."; Biochimica et Biophysica Acta; vol. 22, 1956, pp. 405-411.

Earland, C.; Knight, C.S.; "Studies on the structure of Keratin—The amino acid content of fractions isolated from oxidized wool." Biochimica et Biophysica Acta, vol. 22, 1956, pp. 405- 411.

Ebright, Y.W.; et al; "N-(Iodoacetyl)-p-phenylenediamine-EDTA: A regent for high-efficiency incorporation of an EDTA-metal complex at a rationally selected site within a protein."; Bioconjugate Chemistry; vol. 4 (3), 1993, pp. 219-225.

Edwards, B.; et al; "Chemical studies on powdered keratins." Journal of Biological Chemistry; vol. 154, 1944, pp. 593-596.

Elleman, T.C.; et al; Amino acid sequences of alpha-helical segments from S-carboxymethylkerateine-A. Statistical analysis; Biochemical Journal; vol. 173 (2), 1978, pp. 387-391.

Elleman, T.C.; et al; "Periodicity in high sulphur proteins from wool"; Nature; vol. 246, 1973, pp. 530-531.

Elod, E.: et al.; "Reactions of wool fiber and alterations in the fine structure."; Melliand Textillber; vol. 21, 1940, pp. 385-388.

Elod, E.; et2 al.; The nature of the reactivity of wool. Melliand Textilber; vol. 21, 1940, pp. 617-622.

Elod, E; et al; "The structure and reactivity of the woolen fiber. IX. The effect of H2O2 on wool."; Melliand Textilber; vol. 23, 1942, pp. 313-316.

Elod,E. et al.; "The infiltration of heavy metal sulfides in the keratin fiber." Chem Ber. vol. 74B, 1941, pp. 1759-1762.

Eriksson, A.; et al.; "PDGF $\alpha$- and $\beta$-receptors activate unique and common signal transduction pathaways."; The EMBO Journal; vol. 11, 1992, pp. 543-550.

Filshie, B.K. et al; "The Fine Structure of $\alpha$-Keratin." Journal of Molecular Biology; vol. 3, 1961, pp. 784-786.

Filshie, B.K.; Rodgers, G.E.; "An electron microscope study of the fine structure of feather keratin."; The Journal of Cell Biology; vol. 13, 1962, pp. 1-12.

Frank, S.; et al.; "Transforming growth factors $\beta1$, $\beta2$, and $\beta3$ and their receptors are differentially regulated during normal and impaired wound healing." The Journal of Biological Chemistry; vol. 271, 1996, pp. 10188-10193.

Frankel, M.J.; Powell, B.C.; Ward, K.A.; Sleigh, M.J., Rodgers, G.E.; "The keratin BIIIB gene family: Isolation of cDNA clones and stucture of a gene and a related pseudogene."; Genomics vol. 4, 1989, pp. 182-191.

Fraser, B.R.D, et al; "Intermediate Filaments in $\alpha$-keratins." Proceeedings of the National Academy of Sciences, USA.; Biochemistry; vol. 83, 1986, pp. 1179-1183.

Fraser, R.D.B.; et al; "Microscopic Observations of the Alkaline-Thioglycollate Extraction of Wool."Short Communications, Wool Textile Research Laboratory; vol. 12, 1953, pp. 484-485.

Fraser, R.D.B.; et al; "Disulphide bonding in $\alpha$-keratin."; International Journal of Biological Macromolecules; vol. 10, issue 2, 1988, pp. 106-112.

Fraser, R.D.B.; et al; "Molecular organization in Alpha-Keratin."; Nature; vol. 193, 1962, pp. 1052-1055.

Fraser, R.D.B.; Gillispie, J.M.; "Wool structure and biosysnthesis." Nature vol. 126 1976, pp. 650-654.

Fraser, R.D.B.; Macrae, T.P.; "Helical models of feather keratin structure." Nature; vol. 195, No. 4847, 1962, pp. 1167,1168.

Fraser, R.D.B.; MaCrae, T.P.; Rogers, G.E.; "Structure of Alpha-Keratin." Nature; vol. 183, 1959, pp. 592-594.

Fraser,R.D.B.; Gillespie, J.M.; Macrae,T.P.; "Tyrosine-rich proteins in keratins."; Comparative Biochemistry and Physiology; vol. 44B, 1973, pp. 943-949.

Fratini, A.; et al; "Dietary cysteine regulates the levels of mRNAs encoding a family of cysteine-rich proteins of wool."; Journal of Investigative Dermatology; vol. 102, 1994, pp. 178-185.

Frenkel, M.J. et al.; "Heterogeneity of tyrosine-rich proteins of wool."; Proceedings of the Australian Biochemical Society; vol. 7, 1974, p. 4.

Frenkel, M.J.; "Alkali susceptible amides in tyrosine-rich proteins of wool."; Proceedings of the Australian Biochemical Society; vol. 10, 1977, p. 21.

Frenkel, M.J.; et al.; "Studies of the ribonucleic-acids coding for the keratin complex of hair."; Proceedings of the Australian Biochemical Society; vol. 12, 1979, pp. 87.

Frenkel, M.J.; et al; "Factors influencing biosynthesis of tyrosine-rich proteins of wool."; Australian Journal of Biological Sciences; vol. 27, 1974, pp. 31-38.

Frenkel, M.J.; et al; "The keratin BIIIB gene family: isolation of cDNA clones and structure of a gene and a related pseudogene."; Genomics; vol. 4, No. 2, 1989, pp. 182-191.

Frenkel, M.J.; Gillespie, J.M.; Reis, P.J.; "Studies on the inhibition of synthesis of the tyrosine-rich proteins of wool."; Australian Journal of Biological Sciences; vol. 28, 1975, pp. 331-338.

Frenkel, M.J.; Gillespie, J.M.; Woods, E.F.;"The isolation and properties of a tyrosine-rich protein from wool: component 0.62."; European Journal Biochemistry; vol. 34, 1973, pp. 112-119.

Fujisawa, K.; et al; "Synthesis and characterization of zinc family thiolato complexes.";Abstracts, Symposium on Biofunctional Chemistry, vol. 14, 1999, pp. 52-53.

Gillespie, J.M. et al; "Evidence of homology in a high-sulphur protein fraction (SCMK-B2) of wool and hair α-keratins."; Biochemistry Journal; vol. 110, 1968, pp. 193-198.

Gillespie, J.M. et al; "A comparative study of high-sulphur proteins from α-keratins," Comparative Biochemistry and Physiology; vol. 15, 1965, pp. 175-185.

Gillespie, J.M.; "The isolation from wool of a readily extractable protein of low sulphur content." Biochimica et Biophysica Acta; vol. 27, 1958, pp. 225,226.

Gillespie, J.M.; "The probable role and location of high-glycine-tyrosine proteins in the structure of keratins." Biopolymers, vol. 17, 1978, pp. 2743-2745.

Gillespie, J.M.; "The isolation and properties of some soluble proteins from wool. (II) The preferential extracation of high-sulphur proteins."; Australian Journal of Biological Sciences; vol. 15, No. 1, 1962, pp. 262-277.

Gillespie, J.M.; Broad, A.; "A further study on the dietary-regulated biosynthesis of high-sulphur wool proteins." Biochemistry Journal; vol. 112, 1969, pp. 41-49.

Gillespie, J.M.; Darskus, R.L.; "Relation between the tyrosine content of various wools and their content of a class of protiens rich in tyrosine and glycine."; Australian Journal Biological Science; vol. 24, 1971, pp. 1189-1197.

Gillespie, J.M.; et al.; "Changes in the matrix proteins of wool and mouse hair following the administration of depilatory compounds." Australian Journal of Biological Sciences; vol. 33, 1980, pp. 125-136.

Gillespie, J.M.; et al.; "Proteins of the hard keratins of Echidna, Hedgehog, Rabbit, Ox and Man."; Australian Journal of Biological Sciences, vol. 30, 1977, pp. 401-409.

Gillespie, J.M.; et al; "The Diversity of Keratins"; Comparative Biochemistry and Physiology; vol. 47, No. 2,1974, pp. 339-346.

Gillespie, J.M.; Frenkel, M.J.; "The macroheterogeneity of type I tyrosine-rich proteins of merino wool."; Australian Journal Biological Science; vol. 27, 1974, pp. 617-627.

Japanese Office Action Corresponding to Japanese Patent Application No. 2008-555408; Dispatch Date: Apr. 24, 2012; 3 pages (Foreign Text Only).

WOUND HEALING COMPOSITIONS CONTAINING KERATIN BIOMATERIALS

RELATED APPLICATIONS

This application is a divisional of and claims priority to U.S. patent application Ser. No. 12/104,682, filed Apr. 17, 2008, now allowed, which is a continuation-in-part of Ser. No. 11/676,072, filed Feb. 16, 2007, which claims the benefit under 35 U.S.C. §119(e) of U.S. Provisional Patent Application Ser. No. 60/774,442, filed Feb. 17, 2006, U.S. Provisional Patent Application Ser. No. 60/774,587, filed Feb. 17, 2006, and U.S. Provisional Patent Application Ser. No. 60/774,920, filed Feb. 17, 2006, the disclosures of each of which is incorporated herein by reference in its entirety.

This application also claims the benefit under 35 U.S.C. §119(e) of U.S. Provisional Patent Application Ser. No. 60/912,265, filed Apr. 17, 2007, the disclosure of which is incorporated herein by reference in its entirety.

This application is related to: Ser. No. 11/205,800, titled: Ambient Stored Blood Plasma Expanders, filed Aug. 17, 2005, Ser. No. 11/673,212, titled: Nerve Regeneration Employing Keratin Biomaterials, filed Feb. 9, 2007, and PCT/US2007/004193, titled: Coatings and Biomedical Implants Formed from Keratin Biomaterials, filed Feb. 16, 2007, the disclosures of each of which is incorporated herein by reference in its entirety.

GOVERNMENT SUPPORT

This invention was made with Government support under contract number W81XWH-04-1-0105 from the United States Army. The U.S. Government has certain rights to this invention.

FIELD OF THE INVENTION

The present invention concerns keratin biomaterials and the use thereof in biomedical applications.

BACKGROUND OF THE INVENTION

The earliest documented use of keratin in medicine comes from a Chinese herbalist named Li Shi-Zhen (Ben Cao Gang Mu. Materia Medica, a dictionary of Chinese herbs, written by Li Shi Zhen (1518-1593)). Over a 38-year period, he wrote a collection of 800 books known as the Ben Cao Gang Mu. These books were published in 1596, three years after his death. Among the more than 11,000 prescriptions described in these volumes, is a substance known as Xue Yu Tan, also known as Crinis Carbonisatus, that is made up of ground ash from pyrolized human hair. The stated indications for Xue Yu Tan were accelerated wound healing and blood clotting.

In the early 1800s, when proteins were still being called albuminoids (albumin was a well known protein at that time), many different kinds of proteins were being discovered. Around 1849, the word "keratin" appears in the literature to describe the material that made up hard tissues such as animal horns and hooves (keratin comes from the Greek "kera" meaning horn). This new protein intrigued scientists because it did not behave like other proteins. For example, the normal methods used for dissolving proteins were ineffective with keratin. Although methods such as burning and grinding had been known for some time, many scientists and inventors were more interested in dissolving hair and horns in order to make better products.

During the years from 1905 to 1935, many methods were developed to extract keratins using oxidative and reductive chemistries (Breinl F and Baudisch O, Z physiol Chem 1907; 52:158-69; Neuberg C, U.S. Pat. No. 926,999, Jul. 6, 1909; Lissizin T, Biochem Bull 1915; 4:18-23; Zdenko S, Z physiol Chem 1924; 136:160-72; Lissizin T, Z physiol Chem 1928; 173:309-11). By the late 1920s many techniques had been developed for breaking down the structures of hair, horns, and hooves, but scientists were confused by the behavior of some of these purified proteins. Scientists soon concluded that many different forms of keratin were present in these extracts, and that the hair fiber must be a complex structure, not simply a strand of protein. In 1934, a key research paper was published that described different types of keratins, distinguished primarily by having different molecular weights (Goddard D R and Michaelis L, J Biol Chem 1934; 106:605-14). This seminal paper demonstrated that there were many different keratin homologs, and that each played a different role in the structure and function of the hair follicle.

Earlier work at the University of Leeds and the Wool Industries Research Association in the United Kingdom had shown that wool and other fibers were made up of an outer cuticle and a central cortex. Building on this information, scientists at CSIRO conducted many of the most fundamental studies on the structure and composition of wool. Using X-ray diffraction and electron microscopy, combined with oxidative and reductive chemical methods, CSIRO produced the first complete diagram of a hair fiber (Rivett D E et al., "Keratin and Wool Research," The Lennox Legacy, CSIRO Publishing; Collingwood, VIC, Australia; 1996).

In 1965, CSIRO scientist W. Gordon Crewther and his colleagues published the definitive text on the chemistry of keratins (Crewther W G et al., The Chemistry of Keratins. Anfinsen C B Jr et al., editors. Advances in Protein Chemistry 1965, Academic Press. New York: 191-346). This chapter in *Advances in Protein Chemistry* contained references to more than 640 published studies on keratins. Once scientists knew how to extract keratins from hair fibers, purify and characterize them, the number of derivative materials that could be produced with keratins grew exponentially. In the decade beginning in 1970, methods to form extracted keratins into powders, films, gels, coatings, fibers, and foams were being developed and published by several research groups throughout the world (Anker C A, U.S. Pat. No. 3,642,498, Feb. 15, 1972; Kawano Y and Okamoto S, Kagaku To Seibutsu 1975; 13(5):291-223; Okamoto S, Nippon Shokuhin Kogyo Gakkaishi 1977; 24(1):40-50). All of these methods made use of the oxidative and reductive chemistries developed decades earlier.

In 1982, Japanese scientists published the first study describing the use of a keratin coating on vascular grafts as a way to eliminate blood clotting (Noishiki Y et al., Kobunshi Ronbunshu 1982; 39(4):221-7), as well as experiments on the biocompatibility of keratins (Ito H et al., Kobunshi Ronbunshu 1982; 39(4):249-56). Soon thereafter in 1985, two researchers from the UK published a review article speculating on the prospect of using keratin as the building block for new biomaterials development (Jarman T and Light J, World Biotech Rep 1985; 1:505-12). In 1992, the development and testing of a host of keratin-based biomaterials was the subject of a doctoral thesis for French graduate student Isabelle Valherie (Valherie I and Gagnieu C. Chemical modifications of keratins: Preparation of biomaterials and study of their physical, physiochemical and biological properties. Doctoral thesis. Inst Natl Sci Appl Lyon, France 1992). Soon thereafter, Japanese scientists published a commentary in 1993 on the prominent position keratins could take at the forefront of biomaterials development (Various Authors, Kogyo Zairyo 1993; 41(15) Special issue 2:106-9).

Taken together, the aforementioned body of published work is illustrative of the unique chemical, physical, and biological properties of keratins. However, there remains a great need for optimized keratin preparations for use in biomedical applications, particularly for the treatment of wounds.

SUMMARY OF THE INVENTION

An aspect of the present invention is a pharmaceutical composition comprising a keratin derivative (e.g., keratose, kerateine, or a combination thereof) and optionally, at least one additional active ingredient (e.g., analgesics, antimicrobial agents, additional wound healing agents, etc.).

Another aspect of the present invention is a method for treating a wound (e.g., burns, abrasions, lacerations, incisions, pressure sores, puncture wounds, penetration wounds, gunshot wounds, crushing injuries, etc.) in a subject in need thereof comprising applying a keratin derivative to the wound in an amount effective to treat the wound. In some embodiments, said positively charged composition comprises, consists or consists essentially of a keratose, a kerateine, or combinations thereof.

In some embodiments, the keratin derivative comprises, consists of or consists essentially of alpha keratose, gamma keratose, acidic alpha keratose, basic alpha keratose, acidic gamma keratose, basic gamma keratose, alpha kerateine, gamma kerateine, acidic alpha kerateine, basic alpha kerateine, acidic gamma kerateine, basic gamma kerateine, or combinations thereof.

In some embodiments, the keratin derivative is applied to the wound in an amount effective to inhibit wound conversion, promote wound closure, or both. In some embodiments, the keratin derivative is topically applied. In some embodiments, the keratin derivative is applied by injection into the body of the subject.

A further aspect of the present invention is a method for treating a burn wound in a subject in need thereof comprising applying a keratin derivative to the wound in an amount effective to treat the burn wound. In some embodiments, said positively charged composition comprises, consists or consists essentially of a keratose, a kerateine, or combinations thereof.

In some embodiments, the keratin derivative comprises, consists of or consists essentially of alpha keratose, gamma keratose, acidic alpha keratose, basic alpha keratose, acidic gamma keratose, basic gamma keratose, alpha kerateine, gamma kerateine, acidic alpha kerateine, basic alpha kerateine, acidic gamma kerateine, basic gamma kerateine, or combinations thereof.

In some embodiments, the keratin derivative is applied to the wound in an amount effective to inhibit wound conversion, promote wound closure, or both. In some embodiments, the keratin derivative is topically applied. In some embodiments, the keratin derivative is applied by injection into the body of the subject.

Another aspect of the present invention is a surgical or paramedic aid, comprising: a solid, physiologically acceptable substrate; and a keratin derivative on the substrate. In some embodiments the keratin derivative comprises, consists of or consists essentially of alpha keratose, gamma keratose, acidic alpha keratose, basic alpha keratose, acidic gamma keratose, basic gamma keratose, alpha kerateine, gamma kerateine, acidic alpha kerateine, basic alpha kerateine, acidic gamma kerateine, basic gamma kerateine, or combinations thereof.

A still further aspect of the present invention is a kit comprising a keratin derivative and a container in which said keratin derivative is packaged in sterile form. In some embodiments the keratin derivative comprises, consists of or consists essentially of alpha keratose, gamma keratose, acidic alpha keratose, basic alpha keratose, acidic gamma keratose, basic gamma keratose, alpha kerateine, gamma kerateine, acidic alpha kerateine, basic alpha kerateine, acidic gamma kerateine, basic gamma kerateine, or combinations thereof.

Another aspect of the present invention is the use of a keratin derivative as described herein for the preparation of a composition or medicament for carrying out a method of treatment as described herein, or for making an article of manufacture as described herein.

DETAILED DESCRIPTION OF THE PREFERRED EMBODIMENTS

Figure 1A:
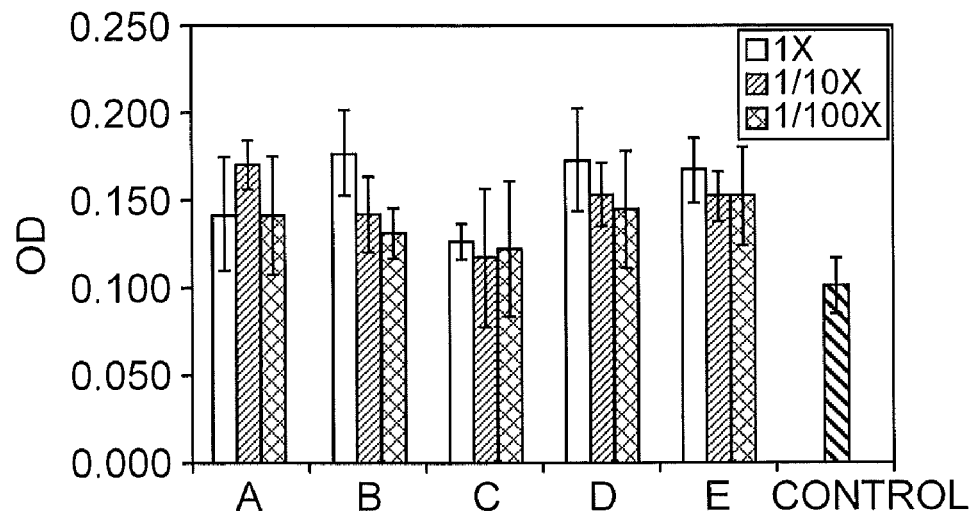
FIG. 1. Skin component cell proliferation. Keratinocytes (a) and fibroblasts (b) treated with soluble keratin biomaterials proliferate more readily than cells treated with media alone.

The disclosures of all cited United States patent references are incorporated herein by reference to the extent they are consistent with the disclosures herein.

The ability of extracted keratin solutions to spontaneously self-assemble at the micron scale was published in two papers in 1986 and 1987 (Thomas H et al., Int J Biol Macromol 1986; 8:258-64; van de Löcht M, Melliand Textilberichte 1987; 10:780-6). This phenomenon is not surprising given the highly controlled superstructure whence hair keratins are obtained. When processed correctly, this ability to self-assemble can be preserved and used to create regular architectures on a size scale conducive to cellular infiltration. When keratins are hydrolyzed (e.g., with acids or bases), their molecular weight is reduced and they lose the ability to self-assemble. Therefore, processing conditions that minimize hydrolysis are preferred.

This ability to self-assemble is a particularly useful characteristic for tissue engineering scaffolds for two reasons. First, self-assembly results in a highly regular structure with reproducible architectures, dimensionality, and porosity. Second, the fact that these architectures form of their own accord under benign conditions allows for the incorporation of cells as the matrix is formed. These two features are critically important to any system that attempts to mimic the native extracellular matrix (ECM).

Cellular recognition is also an important characteristic of biomaterials that seek to mimic the ECM. Such recognition is facilitated by the binding of cell surface integrins to specific amino acid motifs presented by the constituent ECM proteins. Predominant proteins include collagen and fibronectin, both of which have been extensively studied with regard to cell binding. Both proteins contain several regions that support attachment by a wide variety of cell types. It has been shown that, in addition to the widely know Arginine-Glycine-Aspartic Acid (RGD) motif, the "X"-Aspartic Acid-"Y" motif on fibronectin is also recognized by the integrin $\alpha4\beta1$, where X equals Glycine, Leucine, or Glutamic Acid, and Y equals Serine or Valine.

Keratin biomaterials derived from human hair contain these same binding motifs. A search of the NCBI protein database revealed sequences for 71 discrete, unique human hair keratin proteins. Of these, 55 are from the high molecular weight, low sulfur, alpha-helical family. This group of proteins is often referred to as the alpha-keratins and is responsible for imparting toughness to human hair fibers. These alpha-keratins have molecular weights greater than 40 kDa and an average cysteine (the main amino acid responsible for inter- and intramolecular protein bonding) content of 4.8 mole percent. Moreover, analysis of the amino acid sequences of these alpha keratin proteins showed that 78% contain at least one fibronectin-like integrin receptor binding motif, and 25% contain at least two or more. Two recent papers have highlighted the fact that these binding sites are likely present on the surface of keratin biomaterials by demonstrating excellent cell adhesion onto processed keratin foams (Tachibana A et al., J Biotech 2002; 93:165-70; Tachibana A et al., Biomaterials 2005; 26(3):297-302).

Other examples of natural polymers that may be utilized in a similar fashion to the disclosed keratin preparations include, but are not limited to, collagen, gelatin, fibronectin, vitronectin, laminin, fibrin, mucin, elastin, nidogen (entactin), proteoglycans, etc. (See, e.g., U.S. Pat. No. 5,691,203 to Katsuen et al.).

Theories for the biological activity of human hair extracts include that the human hair keratins ("HHKs"), themselves, are biologically active. Over 70 human hair keratins are known and their cDNA-derived sequences published. However, the full compliment of HHKs is unknown and estimates of over 100 have been proposed (Gillespie J M, The structural proteins of hair: isolation characterization, and regulation of biosynthesis. Goldsmith L A (editor), Biochemistry and physiology of the skin (1983), Oxford University Press. New York; 475-510). Within the complete range of HHKs are a small number that have been shown to participate in wound contracture and cell migration (Martin, P, Science 1997; 276: 75-81). In particular, keratins K-6 and K-16 are expressed in the epidermis during wound healing and are also found in the outer root sheath of the hair follicle (Bowden P E, Molecular Aspects of Dermatology (1993), John Wiley & Sons, Inc., Chichester: 19-54). The presence of these HHKs in extracts of human hair, and their subsequent dosing directly into a wound bed, may be responsible for "shortcutting" the otherwise lengthy process of differentiation, migration, and proliferation, or for alleviating some biochemical deficiency, thereby accelerating the tissue repair and regeneration process.

It has been known for more than a decade that growth factors such as bone morphogenetic protein-4 (BMP-4) and other members of the transforming growth factor-$\beta$ (TGF-$\beta$) superfamily are present in developing hair follicles (Jones C M et al., Development 1991; 111:531-42; Lyons K M et al., Development 1990; 109:833-44; Blessings M et al., Genes and Develop 1993; 7:204-15). In fact, more than 30 growth factors and cytokines are involved in the growth of a cycling hair follicle (Hardy M H, Trends Genet 1992; 8(2):55-61; Stenn K S et al., J Dermato Sci 1994; 7S:S109-24; Rogers G E, Int J Dev Biol 2004; 48(2-3):163-70). Many of these molecules have a pivotal role in the regeneration of a variety of tissues. It is highly probable that a number of growth factors become entrained within human hair when cytokines bind to stem cells residing in the bulge region of the hair follicle (Panteleyev A A et al., J Cell Sci 2001; 114:3419-31). These growth factors are predicted to be extracted along with the keratins from end-cut human hair. This observation is not without precedent, as it has previously been shown that many different types of growth factors are present in the extracts of various tissues, and that their activity is maintained even after chemical extraction. Observations such as these show mounting evidence that a number of growth factors may be present in end-cut human hair, and that the keratins may be acting as a highly effective delivery matrix of inter alia, these growth factors.

Keratins are a family of proteins found in the hair, skin, and other tissues of vertebrates. Hair is a unique source of human keratins because it is one of the few human tissues that is readily available and inexpensive. Although other sources of keratins are acceptable feedstocks for the present invention, (e.g. wool, fur, horns, hooves, beaks, feathers, scales, and the like), human hair is preferred for use with human subjects because of its biocompatibility.

Keratins can be extracted from human hair fibers by oxidation or reduction using methods that have been published in the art (See, e.g., Crewther W G et al. The chemistry of keratins, in Advances in Protein Chemistry 1965; 20:191-346). These methods typically employ a two-step process whereby the crosslinked structure of keratins is broken down by either oxidation or reduction. In these reactions, the disulfide bonds in cysteine amino acid residues are cleaved, rendering the keratins soluble (Scheme 1). The cuticle is essentially unaffected by this treatment, so the majority of the keratins remain trapped within the cuticle's protective structure. In order to extract these keratins, a second step using a denaturing solution must be employed. Alternatively, in the case of reduction reactions, these steps can be combined. Denaturing solutions known in the art include urea, transition metal hydroxides, surfactant solutions, and combinations thereof. Preferred methods use aqueous solutions of tris in concentrations between 0.1 and 1.0 M, and urea solutions between 0.1 and 10M, for oxidation and reduction reactions, respectively.

Scheme 1. General representations of (a) oxidation and (b) reduction of disulfide crosslinks in keratin. These reactions cleave the sulfur-sulfur bond in cystine rediudes, thereby destroying the superstructure and rendering the keratins soluble in the reaction media. The resultant fractions are keratose (a) and kerateine (b).

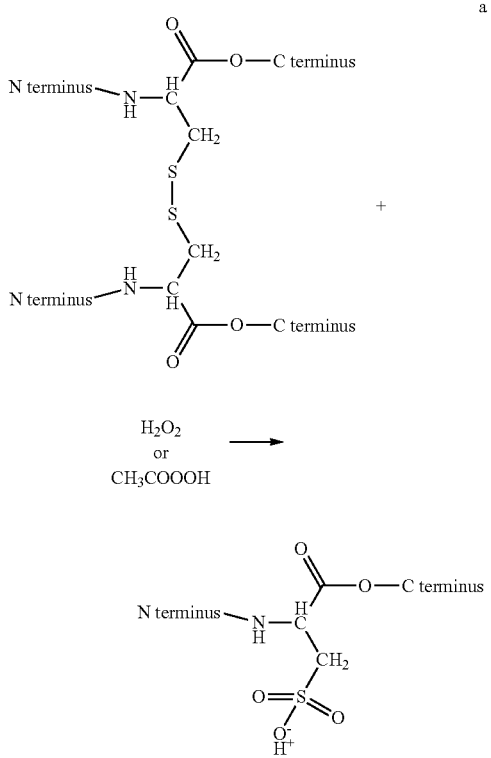

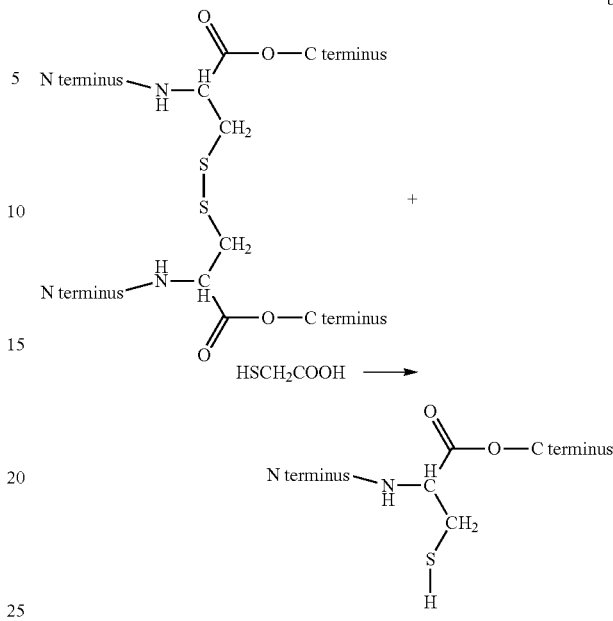

If one employs an oxidative treatment, the resulting keratins are referred to as "keratoses." If a reductive treatment is used, the resulting keratins are referred to as "kerateines" (See Scheme 1)

Crude extracts of keratins, regardless of redox state, can be further refined into "gamma" and "alpha" fractions, e.g., by isoelectric precipitation. High molecular weight keratins, or "alpha keratins," (alpha helical), are thought to derive from the microfibrillar regions of the hair follicle, and typically range in molecular weight from about 40-85 kiloDaltons. Low molecular weight keratins, or "gamma keratins," (globular), are thought to derive from the extracellular matrix regions of the hair follicle, and typically range in molecular weight from about 10-15 kiloDaltons. (See Crewther W G et al. The chemistry of keratins, in Advances in Protein Chemistry 1965; 20:191-346)

Even though alpha and gamma keratins possess unique properties, the properties of subfamilies of both alpha and gamma keratins can only be revealed through more sophisticated means of purification. For example, keratins may be fractionated into "acidic" and "basic" protein fractions. A preferred method of fractionation is ion exchange chromatography. These fractions possess unique properties, such as their differential effects on blood cell aggregation (See Table 1 below; See also: U.S. Patent Application Publication No. 2006/0051732).

"Keratin derivative" as used herein refers to any keratin fractionation, derivative or mixture thereof, alone or in combination with other keratin derivatives or other ingredients, including but not limited to alpha keratose, gamma keratose, alpha kerateine, gamma kerateine, meta keratin, keratin intermediate filaments, and combinations thereof, including the acidic and basic constituents thereof unless specified otherwise, along with variations thereof that will be apparent to persons skilled in the art in view of the present disclosure. In some embodiments, the keratin derivative comprises, consists or consists essentially of a particular fraction or subfraction of keratin. The derivative may comprise, consist or consist essentially of at least 80, 90, 95 or 99 percent by weight of said fraction or subfraction (or more).

In some embodiments, the keratin derivative comprises, consists of, or consists essentially of acidic alpha keratose.

In some embodiments, the keratin derivative comprises, consists of or consists essentially of alpha keratose, where the alpha keratose comprises, consists of or consists essentially of at least 80, 90, 95 or 99 percent by weight of acidic alpha keratose (or more), and where the alpha keratose comprises, consists of or consists essentially of not more than 20, 10, 5 or 1 percent by weight of basic alpha keratose (or less).

In some embodiments, the keratin derivative comprises, consists of, or consists essentially of basic alpha keratose.

In some embodiments, the keratin derivative comprises, consists of or consists essentially of alpha keratose, where the alpha keratose comprises, consists of or consists essentially of at least 80, 90, 95 or 99 percent by weight of basic alpha keratose (or more), and where the alpha keratose comprises, consists of or consists essentially of not more than 20, 10, 5 or 1 percent by weight of acidic alpha keratose (or less).

In some embodiments, the keratin derivative comprises, consists of, or consists essentially of acidic alpha kerateine.

In some embodiments, the keratin derivative comprises, consists of or consists essentially of alpha kerateine, where the alpha kerateine comprises, consists of or consists essentially of at least 80, 90, 95 or 99 percent by weight of acidic alpha kerateine (or more), and where the alpha kerateine comprises, consists of or consists essentially of not more than 20, 10, 5 or 1 percent by weight of basic alpha kerateine (or less).

In some embodiments, the keratin derivative comprises, consists of or consists essentially of basic alpha kerateine.

In some embodiments, the keratin derivative comprises, consists of or consists essentially of alpha kerateine, where the alpha kerateine comprises, consists of or consists essentially of at least 80, 90, 95 or 99 percent by weight of basic alpha kerateine (or more), and where the alpha kerateine comprises, consists of or consists essentially of not more than 20, 10, 5 or 1 percent by weight of acidic alpha kerateine (or less).

In some embodiments, the keratin derivative comprises, consists of or consists essentially of unfractionated alpha+gamma-kerateines. In some embodiments, the keratin derivative comprises, consists of or consists essentially of acidic alpha+gamma-kerateines. In some embodiments, the keratin derivative comprises, consists of or consists essentially of basic alpha+gamma-kerateines.

In some embodiments, the keratin derivative comprises, consists of or consists essentially of unfractionated alpha+gamma-keratose. In some embodiments, the keratin derivative comprises, consists of or consists essentially of acidic alpha+gamma-keratose. In some embodiments, the keratin derivative comprises, consists of or consists essentially of basic alpha+gamma-keratose.

In some embodiments, the keratin derivative comprises, consists of or consists essentially of unfractionated beta-keratose (e.g., derived from cuticle). In some embodiments, the keratin derivative comprises, consists of or consists essentially of basic beta-keratose. In some embodiments, the keratin derivative comprises, consists of or consists essentially of acidic beta-keratose.

The basic alpha keratose is preferably produced by separating basic alpha keratose from a mixture comprising acidic and basic alpha keratose, e.g., by ion exchange chromatography, and optionally the basic alpha keratose has an average molecular weight of from 10 to 100 or 200 kiloDaltons. More preferably, the average molecular weight is from 30 or 40 to 90 or 100 kiloDaltons. Optionally but preferably the process further comprises the steps of re-dissolving said basic alpha-keratose in a denaturing and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of acidic alpha keratose, or less.

The acidic alpha keratose is preferably produced by a reciprocal of the foregoing technique: that is, by separating and retaining acidic alpha keratose from a mixture of acidic and basic alpha keratose, e.g., by ion exchange chromatography, and optionally the acidic alpha keratose has an average molecular weight of from 10 to 100 or 200 kiloDaltons. More preferably, the average molecular weight is from 30 or 40 to 90 or 100 kiloDaltons. Optionally but preferably the process further comprises the steps of re-dissolving said acidic alpha-keratose in a denaturing solution and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of basic alpha keratose, or less.

Basic and acidic fractions of other keratoses can be prepared in like manner as described above for basic and acidic alpha keratose.

The basic alpha kerateine is preferably produced by separating basic alpha kerateine from a mixture of acidic and basic alpha kerateine, e.g., by ion exchange chromatography, and optionally the basic alpha kerateine has an average molecular weight of from 10 to 100 or 200 kiloDaltons. Optionally but preferably the process further comprises the steps of re-dissolving said basic alpha-kerateine in a denaturing and/or buffering solution, optionally in the presence of a chelating agent to complex trace metals, and then re-precipitating the basic alpha kerateine from the denaturing solution. It will be appreciated that the composition preferably contains not more than 5, 2, 1, or 0.1 percent by weight of acidic alpha kerateine, or less.

The acidic alpha kerateine is preferably produced by a reciprocal of the foregoing technique: that is, by separating and retaining acidic alpha kerateine from a mixture of acidic and basic alpha kerateine, e.g., by ion exchange chromatography, and optionally the acidic alpha kerateine has an average molecular weight of from 10 to 100 or 200 kiloDaltons. More preferably, the average molecular weight is from 30 or 40 to 90 or 100 kiloDaltons. Optionally but preferably the process further comprises the steps of re-dissolving said acidic alpha-kerateine in a denaturing and/or buffering solution), optionally in the presence of a chelating agent to complex trace metals, and then re-precipitating the basic alpha kerateine from the denaturing solution. It will be appreciated that the composition preferably contains not more than 5, 2, 1, or 0.1 percent by weight of basic alpha kerateine, or less.

Basic and acidic fractions of other kerateines can be prepared in like manner as described above for basic and acidic alpha kerateine.

Keratin materials are derived from any suitable source including, but not limited to, wool and human hair. In one embodiment keratin is derived from end-cut human hair, obtained from barbershops and salons. The material is washed in hot water and mild detergent, dried, and extracted with a nonpolar organic solvent (typically hexane or ether) to remove residual oil prior to use.

Keratoses. Keratose fractions are obtained by any suitable technique. In one embodiment they are obtained using the method of Alexander and coworkers (P. Alexander et al., *Biochem. J.* 46, 27-32 (1950)). Basically, the hair is reacted with an aqueous solution of peracetic acid at concentrations of less than ten percent at room temperature for 24 hours. The solution is filtered and the alpha-keratose fraction precipitated by addition of mineral acid to a pH of approximately 4. The alpha-keratose is separated by filtration, washed with additional acid, followed by dehydration with alcohol, and then freeze dried. Increased purity can be achieved by re-dissolving the keratose in a denaturing solution such as 7M urea, aqueous ammonium hydroxide solution, or 20 mM tris base buffer solution (e.g., Trizma® base), re-precipitating, re-dissolving, dialyzing against deionized water, and re-precipitating at pH 4.

A preferred method for the production of keratoses is by oxidation with hydrogen peroxide, peracetic acid, or performic acid. A most preferred oxidant is peracetic acid. Preferred concentrations range from 1 to 10 weight/volume percent (w/v %), the most preferred being approximately 2 w/v %. Those skilled in the art will recognize that slight modifications to the concentration can be made to effect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peracetic acid offers the advantages of cost and availability. A preferred oxidation temperature is between 0 and 100 degrees Celsius (° C.). A most preferred oxidation temperature is 37° C. A preferred oxidation time is between 0.5 and 24 hours. A most preferred oxidation time is 12 hours. A preferred liquid to solid ratio is from 5 to 100:1. A most preferred ratio is 20:1. After oxidation, the hair is rinsed free of residual oxidant using a copious amount of distilled water.

The keratoses can be extracted from the oxidized hair using an aqueous solution of a denaturing agent. Protein denaturants are well known in the art, but preferred solutions include urea, transition metal hydroxides (e.g. sodium and potassium hydroxide), ammonium hydroxide, and tris(hydroxymethyl) aminomethane (tris base). A preferred solution is Trizma® base (a brand of tris base) in the concentration range from 0.01 to 1M. A most preferred concentration is 0.1M. Those skilled in the art will recognize that slight modifications to the concentration can be made to effect varying degrees of extraction, with concomitant alterations in reaction time, temperature, and liquid to solid ratio. A preferred extraction temperature is between 0 and 100 degrees Celsius. A most preferred extraction temperature is 37° C. A preferred extraction time is between 0.5 and 24 hours. A most preferred extraction time is 3 hours. A preferred liquid to solid ratio is from 5 to 100:1. A most preferred ratio is 40:1. Additional yield can be achieved with subsequent extractions with dilute solutions of tris base or deionized (DI) water. After extraction, the residual solids are removed from solution by centrifugation and/or filtration.

The crude extract can be isolated by first neutralizing the solution to a pH between 7.0 and 7.4. A most preferred pH is 7.4. Residual denaturing agent is removed by dialysis against DI water. Concentration of the dialysis retentate is followed by lyophilization or spray drying, resulting in a dry powder mixture of both gamma- and alpha-keratose. Alternately, alpha-keratose is isolated from the extract solution by dropwise addition of acid until the pH of the solution reaches approximately 4.2. Preferred acids include sulfuric, hydrochloric, and acetic. A most preferred acid is concentrated hydrochloric acid. Precipitation of the alpha fraction begins at around pH 6.0 and continues until approximately 4.2. Fractional precipitation can be utilized to isolate different ranges of protein with different isoelectric properties. Solid alpha-keratose can be recovered by centrifugation or filtration.

The alpha keratose can be further purified by re-dissolving the solids in a denaturing solution. The same denaturing solutions as those utilized for extraction can be used, however a preferred denaturing solution is tris base. Ethylene diamine tetraacetic acid (EDTA) can be added to complex and remove trace metals found in the hair. A preferred denaturing solution is 20 mM tris base with 20 mM EDTA or DI water with 20 mM EDTA. If the presence of trace metals is not detrimental to the intended application, the EDTA can be omitted. The alpha-keratose is re-precipitated from this solution by dropwise addition of hydrochloric acid to a final pH of approximately 4.2. Isolation of the solid is by centrifugation or filtration. This process can be repeated several times to further purify the alpha-keratose.

The gamma keratose fraction remains in solution at pH 4 and is isolated by addition to a water-miscible organic solvent such as alcohol, followed by filtration, dehydrated with additional alcohol, and freeze dried. Increased purity can be achieved by redissolving the keratose in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and reprecipitating by addition to alcohol. The amount of alcohol consumed in these steps can be minimized by first concentrating the keratose solution by distillation.

After removal of the alpha keratose, the concentration of gamma keratose from a typical extraction solution is approximately 1-2%. The gamma keratose fraction can be isolated by addition to a water-miscible non-solvent. To effect precipitation, the gamma-keratose solution can be concentrated by evaporation of excess water. This solution can be concentrated to approximately 10-20% by removal of 90% of the water. This can be done using vacuum distillation or by falling film evaporation. After concentration, the gamma-keratose solution is added dropwise to an excess of cold non-solvent. Suitable non-solvents include ethanol, methanol, acetone, and the like. A most preferred non-solvent is ethanol. A most preferred method is to concentrate the gamma keratose solution to approximately 10 w/v % protein and add it dropwise to an 8-fold excess of cold ethanol. The precipitated gamma keratose can be isolated by centrifugation or filtration and dried. Suitable methods for drying include freeze drying (lyophilization), air drying, vacuum drying, or spray drying. A most preferred method is freeze drying.

Kerateines. Kerateine fractions can be obtained using a combination of the methods of Bradbury and Chapman (J. Bradbury et al., *Aust. J. Biol. Sci.* 17, 960-72 (1964)) and Goddard and Michaelis (D. Goddard et al., *J. Biol. Chem.* 106, 605-14 (1934)). Essentially, the cuticle of the hair fibers is removed ultrasonically in order to avoid excessive hydrolysis and allow efficient reduction of cortical disulfide bonds in a second step. The hair is placed in a solution of dichloroacetic acid and subjected to treatment with an ultrasonic probe. Further refinements of this method indicate that conditions using 80% dichloroacetic acid, solid to liquid of 1:16, and an ultrasonic power of 180 Watts are optimal (H. Ando et al., *Sen'i Gakkaishi* 31(3), T81-85 (1975)). Solid fragments are removed from solution by filtration, rinsed and air dried, followed by sieving to isolate the hair fibers from removed cuticle cells.

In some embodiments, following ultrasonic removal of the cuticle, alpha- and gamma kerateines are obtained by reaction of the denuded fibers with mercaptoethanol. Specifically, a low hydrolysis method is used at acidic pH (E. Thompson et al., *Aust. J. Biol. Sci.* 15, 757-68 (1962)). In a typical reaction, hair is extracted for 24 hours with 4M mercaptoethanol that has been adjusted to pH 5 by addition of a small amount of potassium hydroxide in deoxygenated water containing 0.02M acetate buffer and 0.001M surfactant.

The solution is filtered and the alpha keratine fraction precipitated by addition of mineral acid to a pH of approximately 4. The alpha keratine is separated by filtration, washed with additional acid, followed by dehydration with alcohol, and then dried under vacuum. Increased purity is achieved by re-dissolving the keratine in a denaturing solution such as 7M urea, aqueous ammonium hydroxide solution, or 20 mM tris buffer solution, re-precipitating, re-dissolving, dialyzing against deionized water, and re-precipitating at pH 4.

The gamma keratine fraction remains in solution at pH 4 and is isolated by addition to a water-miscible organic solvent such as alcohol, followed by filtration, dehydrated with additional alcohol, and dried under vacuum. Increased purity can be achieved by redissolving the keratine in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and reprecipitating by addition to alcohol. The amount of alcohol consumed in these steps can be minimized by first concentrating the keratin solution by distillation.

In an alternate method, the keratine fractions are obtained by reacting the hair with an aqueous solution of sodium thioglycolate.

A preferred method for the production of keratines is by reduction of the hair with thioglycolic acid or beta-mercaptoethanol. A most preferred reductant is thioglycolic acid (TGA). Preferred concentrations range from 1 to 10M, the most preferred being approximately 1.0M. Those skilled in the art will recognize that slight modifications to the concentration can be made to effect varying degrees of reduction, with concomitant alterations in pH, reaction time, temperature, and liquid to solid ratio. A preferred pH is between 9 and 11. A most preferred pH is 10.2. The pH of the reduction solution is altered by addition of base. Preferred bases include transition metal hydroxides, sodium hydroxide, and ammonium hydroxide. A most preferred base is sodium hydroxide. The pH adjustment is effected by dropwise addition of a saturated solution of sodium hydroxide in water to the reductant solution. A preferred reduction temperature is between 0 and 100° C. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1. Unlike the previously described oxidation reaction, reduction is carried out at basic pH. That being the case, keratins are highly soluble in the reduction media and are expected to be extracted. The reduction solution is therefore combined with the subsequent extraction solutions and processed accordingly.

Reduced keratins are not as hydrophilic as their oxidized counterparts. As such, reduced hair fibers will not swell and split open as will oxidized hair, resulting in relatively lower yields. Another factor affecting the kinetics of the reduction/extraction process is the relative solubility of keratines. The relative solubility rankings in water is gamma-keratose>alpha-keratose>gamma-keratine>alpha-keratine from most to least soluble. Consequently, extraction yields from reduced hair fibers are not as high. This being the case, subsequent extractions are conducted with additional reductant plus denaturing agent solutions. Preferred solutions for subsequent extractions include TGA plus urea, TGA plus tris base, or TGA plus sodium hydroxide. After extraction, crude fractions of alpha- and gamma-keratine can be isolated using the procedures described for keratoses. However, precipitates of gamma- and alpha-keratine re-form their cystine crosslinks upon exposure to oxygen. Precipitates must therefore be re-dissolved quickly to avoid insolubility during the purification stages, or precipitated in the absence of oxygen.

Residual reductant and denaturing agents can be removed from solution by dialysis. Typical dialysis conditions are 1 to 2% solution of keratines dialyzed against DI water for 24 to 72 hours. Those skilled in the art will recognize that other methods exist for the removal of low molecular weight contaminants in addition to dialysis (e.g. microfiltration, chromatography, and the like). The use of tris base is only required for initial solubilization of the keratines. Once dissolved, the keratines are stable in solution without the denaturing agent. Therefore, the denaturing agent can be removed without the resultant precipitation of keratines, so long as the pH remains at or above neutrality. The final concentration of keratines in these purified solutions can be adjusted by the addition/removal of water.

Regardless of the form of the keratin (i.e. keratoses or keratines), several different approaches to further purification can be employed to keratin solutions. Care must be taken, however, to choose techniques that lend themselves to keratin's unique solubility characteristics. One of the most simple separation technologies is isoelectric precipitation. In this method, proteins of differing isoelectric point can be isolated by adjusting the pH of the solution and removing the precipitated material. In the case of keratins, both gamma- and alpha-forms are soluble at pH>6.0. As the pH falls below 6, however, alpha-keratins begin to precipitate. Keratin fractions can be isolated by stopping the precipitation at a given pH and separating the precipitate by centrifugation and/or filtration. At a pH of approximately 4.2, essentially all of the alpha-keratin will have been precipitated. These separate fractions can be re-dissolved in water at neutral pH, dialyzed, concentrated, and reduced to powders by lyophilization or spray drying. However, keratine fractions must be stored in the absence of oxygen or in dilute solution to avoid crosslinking.

Another general method for separating keratins is by chromatography. Several types of chromatography can be employed to fractionate keratin solutions including size exclusion or gel filtration chromatography, affinity chromatography, isoelectric focusing, gel electrophoresis, ion exchange chromatography, and immunoaffinity chromatography. These techniques are well known in the art and are capable of separating compounds, including proteins, by the characteristics of molecular weight, chemical functionality, isoelectric point, charge, or interactions with specific antibodies, and can be used alone or in any combination to effect high degrees of separation and resulting purity.

A preferred purification method is ion exchange (IEx) chromatography. IEx chromatography is particularly suited to protein separation owning to the amphiphilic nature of proteins in general and keratins in particular. Depending on the starting pH of the solution, and the desired fraction slated for retention, either cationic or anionic IEx (CIEx or AIEx, respectively) techniques can be used. For example, at a pH of 6 and above, both gamma- and alpha-keratins are soluble and above their isoelectric points. As such, they are anionic and can be bound to an anionic exchange resin. However, it has been discovered that a sub-fraction of keratins does not bind to a weakly anionic exchange resin and instead passes through a column packed with such resin. A preferred solution for AIEx chromatography is purified or fractionated keratin, isolated as described previously, in purified water at a concentration between 0 and 5 weight/volume %. A preferred concentration is between 0 and 4 w/v %. A most preferred concentration is approximately 2 w/v %. It is preferred to keep the ionic strength of said solution initially quite low to facilitate binding to the AIEx column. This is achieved by using a minimal amount of acid to titrate a purified water solution of the keratin to between pH 6 and 7. A most preferred pH is 6. This solution can be loaded onto an AIEx column such as DEAE-Sepharose® resin or Q-Sepharose® resin columns. A preferred column resin is DEAE-Sepharose® resin. The solution that passes through the column can be collected and further processed as described previously to isolate a fraction of acidic keratin powder.

In some embodiments the activity of the keratin matrix is enhanced by using an AIEx column to produce the keratin to thereby promote cell adhesion. Without wishing to be bound to any particular theory, it is envisioned that the fraction that passes through an anionic column, i.e. acidic keratin, promotes cell adhesion.

Another fraction binds readily, and can be washed off the column using salting techniques known in the art. A preferred elution medium is sodium chloride solution. A preferred concentration of sodium chloride is between 0.1 and 2M. A most preferred concentration is 2M. The pH of the solution is preferred to be between 6 and 12. A most preferred pH is 12. In order to maintain stable pH during the elution process, a buffer salt can be added. A preferred buffer salt is Trizma® base. Those skilled in the art will recognize that slight modifications to the salt concentration and pH can be made to effect the elution of keratin fractions with differing properties. It is also possible to use different salt concentrations and pH's in sequence, or employ the use of salt and/or pH gradients to produce different fractions. Regardless of the approach taken, however, the column eluent can be collected and further processed as described previously to isolate fractions of basic keratin powders.

A complimentary procedure is also feasible using CIEx techniques. Namely, the keratin solution can be added to a cation exchange resin such as SP Sepharose® resin (strongly cationic) or CM Sepharose® resin (weakly cationic), and the basic fraction collected with the pass through. The retained acid keratin fraction can be isolated by salting as previously described.

Meta Keratins. Meta keratins are synthesized from both the alpha and gamma fractions of kerateine using substantially the same procedures. Basically, the kerateine is dissolved in a denaturing solution such as 7M urea, aqueous ammonium hydroxide solution, or 20 mM tris buffer solution. Pure oxygen is bubbled through the solution to initiate oxidative coupling reactions of cysteine groups. The progress of the reaction is monitored by an increase in molecular weight as measured using SDS-PAGE. Oxygen is continually bubbled through the reaction solution until a doubling or tripling of molecular weight is achieved. The pH of the denaturing solution can be adjusted to neutrality to avoid hydrolysis of the proteins by addition of mineral acid.

Keratin Intermediate Filaments. IFs of human hair fibers are obtained using the method of Thomas and coworkers (H. Thomas et al., *Int. J. Biol. Macromol*, 8, 258-64 (1986)). This is essentially a chemical etching method that reacts away the keratin matrix that serves to "glue" the IFs in place, thereby leaving the IFs behind. In a typical extraction process, swelling of the cuticle and sulfitolysis of matrix proteins is achieved using 0.2M $Na_2SO_3$, 0.1M $Na_2O_6S_4$ in 8M urea and 0.1M tris-HCl buffer at pH 9. The extraction proceeds at room temperature for 24 hours. After concentrating, the dissolved matrix keratins and IFs are precipitated by addition of zinc acetate solution to a pH of approximately 6. The IFs are then separated from the matrix keratins by dialysis against 0.05M tetraborate solution. Increased purity is obtained by precipitating the dialyzed solution with zinc acetate, redissolving the IFs in sodium citrate, dialyzing against distilled water, and then freeze drying the sample.

Further discussion of keratin preparations are found in U.S. Patent Application Publication 2006/0051732 (Van Dyke), which is incorporated by reference herein.

Compositions and formulations. Dry powders may be formed of keratin derivatives as described above in accordance with known techniques such as freeze drying (lyophilization). In some embodiments, compositions of the invention may be produced by mixing such a dry powder composition form with an aqueous solution to produce a composition comprising an electrolyte solution having said keratin derivative solubilized therein. The mixing step can be carried out at any suitable temperature, typically room temperature, and can be carried out by any suitable technique such as stirring, shaking, agitation, etc. The salts and other constituent ingredients of the electrolyte solution (e.g., all ingredients except the keratin derivative and the water) may be contained entirely in the dry powder, entirely within the aqueous composition, or may be distributed between the dry powder and the aqueous composition. For example, in some embodiments, at least a portion of the constituents of the electrolyte solution are contained in the dry powder.

The formation of a matrix comprising keratin materials such as described above can be carried out in accordance with techniques long established in the field or variations thereof that will be apparent to those skilled in the art. In some embodiments, the keratin preparation is dried and rehydrated prior to use. See, e.g., U.S. Pat. No. 2,413,983 to Lustig et al., U.S. Pat. No. 2,236,921 to Schollkipf et al., and U.S. Pat. No. 3,464,825 to Anker. In preferred embodiments, the matrix, or hydrogel, is formed by re-hydration of the lyophilized material with a suitable solvent, such as water or phosphate buffered saline (PBS). The gel can be sterilized, e.g., by γ-irradiation (800 krad) using a Co60 source. Other suitable methods of forming keratin matrices include, but are not limited to, those found in U.S. Pat. Nos. 6,270,793 (Van Dyke et al.), 6,274,155 (Van Dyke et al.), 6,316,598 (Van Dyke et al.), 6,461,628 (Blanchard et al.), 6,544,548 (Siller-Jackson et al.), and 7,01,987 (Van Dyke).

In some composition embodiments, the keratin derivatives (particularly alpha and/or gamma kerateine and alpha and/or gamma keratose) have an average molecular weight of from about 10 to 70 or 85 or 100 kiloDaltons. Other keratin derivatives, particularly meta-keratins, may have higher average molecular weights, e.g., up to 200 or 300 kiloDaltons. In general, the keratin derivative (this term including combinations of derivatives) may be included in the composition in an amount of from about 0.1, 0.5 or 1 percent by weight up to 3, 4, 5, or 10 percent by weight. The composition when mixed preferably has a viscosity of about 1 or 1.5 to 4, 8, 10 or 20 centipoise. Viscosity at any concentration can be modulated by changing the ratio of alpha to gamma keratose.

The keratin derivative composition or formulation may optionally contain one or more active ingredients such as one or more growth factors, analgesics, antimicrobials, additional coagulants, etc. (e.g., in an amount ranging from 0.0000001 to 1 or 5 percent by weight of the composition that comprises the keratin derivative(s)), to facilitate growth or healing, provide pain relief, inhibit the growth of microbes such as bacteria, facilitate or inhibit coagulation, facilitate or inhibit cell or tissue adhesion, etc. Examples of suitable growth factors include, but are not limited to, nerve growth factor, vascular endothelial growth factor, fibronectin, fibrin, laminin, acidic and basic fibroblast growth factors, testosterone, ganglioside GM-1, catalase, insulin-like growth factor-I (IGF-I), platelet-derived growth factor (PDGF), neuronal growth factor galectin-1, and combinations thereof. See, e.g., U.S. Pat. No. 6,506,727 to Hansson et al. and U.S. Pat. No. 6,890,531 to Horie et al.

As used herein, "growth factors" include molecules that promote the regeneration, growth and survival of tissue. Growth factors that are used in some embodiments of the present invention may be those naturally found in keratin extracts, or may be in the form of an additive, added to the keratin extracts or formed keratin matrices. Examples of growth factors include, but are not limited to, nerve growth factor (NGF) and other neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), epidermal growth factor (EGF), hepatocyte growth factor (HGF), granulocyte-colony stimulating factor (G-CSF), and granulocyte-macrophage colony stimulating factor (GM-CSF). There are many structurally and evolutionarily related proteins that make up large families of growth factors, and there are numerous growth factor families, e.g., the neurotrophins (NGF, BDNF, and NT3). The neurotrophins are a family of molecules that promote the growth and survival of, inter alia, nervous tissue. Examples of neurotrophins include, but are not limited to, nerve growth factor (NGF), brain-derived neurotrophic factor (BDNF), neurotrophin 3 (NT-3), and neurotrophin 4 (NT-4). See U.S. Pat. Nos. 5,843,914 to Johnson, Jr. et al.; 5,488,099 to Persson et al.; 5,438,121 to Barde et al.; 5,235,043 to Collins et al.; and 6,005,081 to Burton et al.

For example, a growth factor can be added to the keratin matrix composition in an amount effective to promote the regeneration, growth and survival of various tissues. The growth factor is provided in concentrations ranging from 0.1 ng/mL to 1000 ng/mL. More preferably, growth factor is provided in concentrations ranging from 1 ng/mL to 100 ng/mL, and most preferably 10 ng/mL to 100 ng/mL. See U.S. Pat. No. 6,063,757 to Urso.

The composition is preferably sterile and non-pyrogenic. The composition may be provided preformed and aseptically packaged in a suitable container, such as a flexible polymeric bag or bottle, or a foil container, or may be provided as a kit of sterile dry powder in one container and sterile aqueous solution in a separate container for mixing just prior to use. When provided pre-formed and packaged in a sterile container, the composition preferably has a shelf life of at least 4 or 6 months (up to 2 or 3 years or more) at room temperature, prior to substantial loss of viscosity (e.g., more than 10 or 20 percent) and/or substantial precipitation of the keratin derivative (e.g., settling detectable upon visual inspection). The kit may contain a single unit dose of the active keratin derivative. A single unit dose may be 0.1 or 0.5 or 1, to 100 or 200 or 300 grams of the keratin derivative, or more, depending upon its intended use.

Other examples of natural polymers that may be utilized in a similar fashion to the disclosed keratin preparations include, but are not limited to, collagen, gelatin, fibronectin, vitronectin, laminin, fibrin, mucin, elastin, nidogen (entactin), proteoglycans, etc. (See, e.g., U.S. Pat. No. 5,691,203 to Katsuen et al.).

Clotting compositions and methods to control bleeding containing keratin biomaterials. One aspect of the present invention is a method for treating bleeding in a subject afflicted with a bleeding wound comprising: applying a keratin derivative to a bleeding wound in an amount effective to treat the bleeding. In some embodiments, the keratin derivative comprises, consists of or consists essentially of kerateine, alpha kerateine, gamma kerateine, acidic alpha kerateine, basic alpha kerateine, or combinations thereof, such as described above. The bleeding may be that associated with, e.g., severe trauma producing rapid, voluminous hemorrhaging, including, but not limited to: surgery; penetrating trauma such as stabbing and gunshot wounds; motor vehicle trauma; and head, neck, chest and abdominal hemorrhaging; with or without clear access to the site of the hemorrhaging.

Many different compositions may comprise the hemostatic agent, including, but not limited to, keratin derivatives. Other examples of hemostatic agents include, but are not limited to, those comprising fibrin or fibrinogen, thrombin, factor XIII, calcium, chitosan (deacetylated poly-N-acetyl glucosamine), zeolite (oxides of silicon, aluminum, sodium, magnesium, and quartz), chitin (acetylated poly-N-acetyl glucosamine), bovine clotting factors, non-zeolite mineral (e.g., hydrophobic polymers and potassium salts), and molecular sieve materials from plant sources (e.g., TraumaDEX™, Arista™ AH, etc., Medafor, Inc., Minneapolis, Minn.). It should be noted, however, that not all of these hemostatic agents are recommended for all types of bleeding treatments, and those skilled in the art should select hemostatic agents for use in the disclosed compositions and methods accordingly. For example, zeolite is intended only for external use.

In some embodiments of the invention, gels containing keratin derivatives are used. The gels of these embodiments are adherent to the tissue and hydrophilic. In some embodiments, when deposited onto a bleeding surface of a wound, the gels are sufficiently adhesive to not be washed away, even in the presence of active bleeding. In some embodiments the gel absorbs fluid from the blood and becomes even more adherent (e.g., within minutes of administration). Contact of the gel of some embodiments with blood can instigate thrombus formation, probably through platelet activation and/or concentration of clotting factors. Also, without wishing to be bound to any particular theory, it is thought that the adherent gel of some embodiments can form a physical seal of the wound site and provide a porous scaffold for cell infiltration and granulation-like tissue formation, much like clotted blood.

In some embodiments, the keratin composition is applied directly onto the site of the bleeding. In some embodiments, the keratin composition is injected into the body of a subject to treat an internal site of bleeding, e.g., where there is no clear access to the site of hemorrhaging.

Wound healing compositions containing keratin biomaterials and methods to promote wound healing. An aspect of the present invention is a method of treating a wound (e.g., burns, abrasions, lacerations, incisions, pressure sores, puncture wounds, penetration wounds, gunshot wounds, crushing injuries, etc.) in a subject in need thereof, comprising: topically applying a keratin derivative to the wound in an amount effective to treat the wound. In some embodiments the keratin derivative comprises, consists of or consists essentially of keratose, alpha keratose, gamma keratose, acidic alpha keratose, acidic gamma keratose, basic alpha keratose, basic gamma keratose, kerateine, alpha kerateine, gamma kerateine, acidic alpha kerateine, acidic gamma kerateine, basic alpha kerateine, basic gamma kerateine, etc., or combinations thereof, such as described above.

The keratin derivative can be topically applied as a dry powder formulation or, in some embodiments, applied in an aqueous carrier (e.g., in the form of a gel). In some embodiments, the keratin derivative is provided in an ointment (a water-in-oil preparation in which the amount of oil exceeds the amount of water in the emulsion), or in a cream (an oil-in water preparation in which the amount of water is equal to or exceeds the amount of oil in the emulsion). In some embodiments, the keratin derivative is injected under the skin to reach an internal site of injury.

"Subjects" (or "patients") to be treated with the methods and compositions described herein include both human subjects and animal subjects (particularly other mammalian subjects such as dogs, cats, horses, monkeys, etc.) for veterinary purposes. Human subjects are particularly preferred. The subjects may be male or female and may be any age, including neonate, infant, juvenile, adolescent, adult, and geriatric subjects.

Examples of wounds that can be treated with the present invention include burn wounds. Burn wounds are tissue injuries that can result from heat, chemicals, sunlight, electricity, radiation, etc. Burns caused by heat, or thermal burns, are the most common. Chemical burns resemble thermal burns. Though burn wounds tend to occur most often on the skin, other body structures may be affected. For example, a severe burn may penetrate down to the fat, muscle or bone.

Wounds are often characterized by the depth of injury. For example, the degree of a burn is characterized as first, second or third depending on the depth of the tissues injured. In a first-degree burn, only the top layer of skin (the epidermis) is damaged. In second-degree burns, the middle layer of skin (the dermis) is damaged. Finally, in a third-degree burn, the most severe type, the damage is deep enough to affect the inner (fat) layer of the skin. Similarly, pressure sores of the skin are characterized as stage I (red, unbroken skin, erythema does not fade with release of pressure), stage II (disrupted epidermis, often with invasion into the dermis), stage III (injury of the dermis), and stage 1V (subcutaneous tissue is exposed).

In pressure sore wounds, pressure-induced constriction of local capillaries results in ischemia in the affected skin. Similarly, a burn wound is ischemic due to associated capillary thrombosis. A diabetic ulcer is another example of a poorly perfused wound. For these types of wounds, where blood is not readily available to aid in the normal course of wound healing, in some embodiments compositions containing keratin derivatives are useful not only for providing a physical seal of the wound site, but also for providing a porous scaffold for cell infiltration and granulation-like tissue formation, much like clotted blood.

Wounds can be evolving injuries in that the area of tissue damage grows after the initial insult. For example, a burn wound is typically an evolving injury characterized by three zones: the zone of necrosis, the zone of injury, and the zone of hyperemia. The zone of necrosis is the area that directly received the external insult (e.g., heat or chemical insult), and contains irreversibly damaged tissue. The zone of injury is peripheral to and below the zone of necrosis, and the tissue is initially viable but fragile. In a typical burn, the area of the zone of necrosis increases as the tissue in the zone of injury becomes damaged. The term "wound conversion" describes the process by which the zone of injury progresses to the zone of necrosis, increasing the overall area of the wound. See, e.g., U.S. Pat. No. 5,583,126 to Daynes et al. The zone of hyperemia is peripheral to and below the zone of injury. It has minimal cell injury, but is vasodilated.

Without wishing to be bound to any particular theory, it is thought that the keratin derivatives disclosed herein both suppress wound growth due to wound conversion (e.g., measured by area of the wound over time, determined by observations of the severity of tissue damage with and/or without treatment, etc.) and promote and/or accelerate the healing of wounds (e.g., the measured wound area decreases at a faster rate over time with treatment, the wound is observed to be healing at a faster rate upon treatment, etc.). The normal course of healing for superficial and partial-thickness wounds is by regeneration of epithelium from existing basal cells at the surface of the wound, with or without mild contraction. Deep wounds heal by a combination of regeneration of epithelium and contraction. Contraction serves to decrease the area of the wound, and the epithelium regenerates from the margins of the wound.

In some embodiments, the keratin biomaterials are useful in promoting wound healing by enhancing the proliferation of fibroblasts (e.g., dermal fibroblasts) and/or keratinocytes (e.g., epidermal keratinocytes). See, e.g., U.S. Pat. No. 6,673, 603 to Baetge et al. and U.S. Pat. No. 5,840,309 to Herstein et al. Without wishing to be bound to any particular theory, it is thought that the enhancement of fibroblast and/or keratinocyte proliferation is promoted by growth factors naturally found within the keratin preparations.

In some types of wounds, treatment includes the control of bleeding. For instance, abrasions, lacerations, incisions, penetration wounds, and crushing injuries, etc. often involve bleeding. Crushing injuries, for example, may involve an open wound (i.e., where the skin is torn and tissues are exposed to the environment), or a closed wound (i.e., where the skin is intact, but the underlying tissue is damaged).

Abrasions are superficial wounds in which the epidermis of the skin is scraped off. Abrasions can be caused by, e.g., falling upon a rough surface. Lacerations are typically irregular wounds caused by, e.g., a blunt impact to soft tissue (e.g., skin) that lies on top of hard tissue (e.g., bone), or involves the tearing of soft tissues (e.g., lacerations associated with childbirth). Lacerations typically show bridging, where connective tissue and/or blood vessels flatten against the surface of the underlying hard tissue. Sometimes injury caused by sharp objects is also termed a laceration. In the case of injury caused by a sharp object, there is normally no bridging because the connective tissue and blood vessels are severed.

Incisions or incised wounds are normally caused by clean, sharp-edged objects. Superficial incisions (involving only the epidermis) are typically referred to as "cuts." Incisions may be caused by a knife, razor, glass splinter, etc., or may be caused by a scalpel during surgery or other medical procedure. Penetration wounds are caused by objects entering the body (e.g., a knife). Puncture wounds are caused by objects penetrating the skin, such as a needle or nail. Gunshot wounds are caused by bullets entering, driving through, and sometimes exiting, the body.

Wound injuries carry a risk of infection. In some embodiments, the wound healing composition includes an antimicrobial agent. Examples of antimicrobial agents that can be topically applied include, but are not limited to, bacitracin (e.g., 400-500 U/g of ointment), polymyxin B sulfate (e.g., 5,000 or 10,000 U/g of ointment), neomycin (e.g., 3.5 mg/g of ointment), Polysporin® antibiotic (a blend of polymyxin B sulfate and bacitracin in an ointment base), Neosporin® antibiotic (a blend of neomycin, bacitracin and polymyxin B sulfate in an ointment base), povidone-iodine, silver sulfadiazine (e.g., 1% cream), mafenide acetate (a methylated topical sulfonamide compound, e.g., as a 0.5% cream), nystatin (a fungicide), nitrofurazone (e.g., 0.2%) and gentamicin (e.g., 0.1% cream). Antimicrobial solutions include, but are not limited to, acetic acid (e.g., 0.5% or 0.25%), sodium hypochlorite (Dakin's solution, e.g., 0.5% or 0.25% NaOCl), silver nitrate (e.g., 0.5%), and chlorhexidine gluconate (e.g., 0.5%). In some embodiments, the wound healing composition includes additional wound healing components. Some antimicrobials are thought to also promote wound healing by mechanisms apart from their effects as a bactericide or fungicide, etc. For example, there is evidence that silver sulfadizine, the most commonly used topical agent for burn care in the United States, has this dual action (Ward R S and Saffle J R, Physical Therapy 1995; 75(6) 526-38).

In some embodiments, the wound healing composition includes analgesics or anesthetics for pain relief, surfactants, anti-inflammatory agents, etc. See, e.g., U.S. Pat. No. 6,562,326 to Miller.

The keratin compositions disclosed herein are useful in both controlling the bleeding and in promoting the healing of wounds. The compositions are useful for both open wounds and closed wounds. In the case of closed wounds, the keratin may be applied into the wound site by, for example, injection with a syringe or from a pressurized canister. In the case of blunt trauma, the keratin compositions can be, for example, injected into the abdomen through the skin into the site of internal bleeding. However, as those skilled in the art will appreciate, tissue swelling must be taken into account so as to avoid over-expansion and possible tissue and/or organ damage. Methods of attenuating swelling, such as treatment with cold (e.g., cool water, ice, etc.) and elevation of the affected area, may also be used.

The dose of the keratin material applied to the wound will depend upon the particular wound suffered, the age and overall condition of the subject, the route of administration, etc., and can be optimized in accordance with known techniques. In some embodiments, the dosage is 0.1 or 0.5 or 1, to 100 or 200 or 300 grams of the keratin derivative, or more (e.g., in powder or aqueous carrier), depending upon its intended use. In some embodiments, the keratin is provided at a concentration from 0.001 to 10 mg/mL, or from 0.01 to 5 mg/mL. In some embodiments, the keratin is provided at a concentration of from 0.1% to 80% (w/v), or from 1% to 50% (w/v), or from 5% to 30% (w/v).

In some embodiments, the wound is treated by application of a keratin preparation in the form of a gel, cream or ointment. The would may also be treated by a "wet-to-moist" dressing, where the keratin (and optionally other additives) is generally added in its powder form to an aqueous carrier (e.g., distilled water or saline), and a dressing (e.g., gauze) is soaked with the aqueous preparation and placed onto the wound. The aqueous preparation should be reapplied as necessary to prevent the dressing from drying. Alternatively, the keratin preparation can be formed as a sheet wound dressing as described in U.S. Pat. No. 6,274,163 to Blanchard et al. In further embodiments, the keratin preparation is formulated for use as a spray, e.g., solutions such as aqueous preparations that can be sprayed upon the wound with an aerosol pump.

In some embodiments, the wound is treated by reapplication of the disclosed compositions, e.g., several times a day, or as needed. Cleansing to remove bacteria and debridement to remove necrotic debris may also be warranted during the course of treatment. Application of a moisturizing cream or ointment may be used to soften wound eschar in order to assist in debridement.

Surgical or paramedic aids. Another aspect of the invention is a surgical or paramedic aid that includes a solid, physiologically acceptable substrate and a keratin derivative on said substrate. "Substrate" includes sponges, packings, wound dressings (such as gauze or bandages), sutures, fabrics, and prosthetic devices.

Kits comprising keratin derivatives. Another aspect of the invention is a kit comprising, consisting of, or consisting essentially of a keratin derivative in a container. The keratin derivative is preferably packaged in the container in sterile form. The kit may include a physiologically acceptable substrate, such as sponges, packings, wound dressings (such as gauze or bandages), sutures, fabrics, and prosthetic devices.

Embodiments of the invention are further described in the following non-limiting examples.

EXAMPLE 1

Keratin Derivatives/Fractions

Keratose fractions were obtained using a method based on that of Alexander and coworkers. However the method was substantially modified to minimize hydrolysis of peptide bonds. Briefly, 50 grams of clean, dry hair that was collected from a local barber shop was reacted with 1000 mL of an aqueous solution of 2 w/v % peracetic acid (PAA) at room temperature for 12 hr. The oxidized hair was recovered using a 500 micron sieve, rinsed with copious amounts of DI water, and the excess water removed. Keratoses were extracted from the oxidized hair fibers with 1000 mL of 100 mM Trizma® base. After 3 hours, the hair was separated by sieve and the liquid neutralized by dropwise addition of hydrochloric acid (HCl). Additional keratoses were extracted from the remaining hair with two subsequent extractions using 1000 mL of 0.1M Trizma® base and 1000 mL of DI water, respectively. Each time the hair was separated by sieve and the liquid neutralized with HCl. All three extracts were combined, centrifuged, and any residual solid material removed by filtration. The combined extract was purified by tangential flow dialysis against DI water with a 1 KDa nominal low molecular weight cutoff membrane. The solution was concentrated and lyophilized to produce a crude keratose powder.

Keratine fractions were obtained using a modification of the method described by Goddard and Michaelis (J Biol Chem 1934; 106:605-14). Briefly, the hair was reacted with an aqueous solution of 1M TGA at 37° C. for 24 hours. The pH of the TGA solution had been adjusted to pH 10.2 by dropwise addition of saturated NaOH solution. The extract solution was filtered to remove the reduced hair fibers and retained. Additional keratin was extracted from the fibers by sequential extractions with 1000 mL of 100 mM TGA at pH 10.2 for 24 hours, 1000 mL of 10 mM TGA at pH 10.2 for 24 hours, and DI water at pH 10.2 for 24 hours. After each extraction, the solution was centrifuged, filtered, and added to the dialysis system. Eventually, all of the extracts were combined and dialyzed against DI water with a 1 KDa nominal low molecular weight cutoff membrane. The solution was concentrated, titrated to pH 7, and stored at approximately 5% total protein concentration at 4° C. Alternately, the concentrated solution could be lyophilized and stored frozen and under nitrogen.

Just prior to fractionation, keratose samples were re-dissolved in ultrapure water and titrated to pH 6 by addition of dilute HCl solution. Keratine samples were titrated to pH 6 by careful addition of dilute HCl solution as well. The samples were loaded onto a 200 mL flash chromatography column containing either DEAE-Sepharose® (weakly anionic) or Q-Sepharose® (strongly anionic) exchange resin (50-100 mesh; Sigma-Aldrich, Milwaukee, Wis.) with gentle pressure and the flow through collected (acidic keratin). A small volume of 10 mM Trizma® base (approximately 200 mL) at pH 6 was used to completely wash through the sample. Basic keratin was eluted from the column with 100 mM tris base plus 2M NaCl at pH 12. Each sample was separately neutralized and dialyzed against DI water using tangential flow dialysis with a LMWCO of 1 KDa, concentrated by rotary evaporation, and freeze dried.

As previously described, a sample of alpha-keratose was produced, separated on a DEAE-Sepharose® IEx column into acidic and basic fractions, dissolved in PBS, and the pH adjusted to 7.4. These solutions were prepared at 5 weight percent concentration and their red blood cell (RBC) aggregation characteristics grossly evaluated with fresh whole human blood by mixing at a 1:1 ratio. Samples were taken after 20 minutes and evaluated by light microscopy. The ion exchange chromatography was highly effective at separating the aggregation phenomenon (data not shown). Basic alpha-keratose was essentially free from interactions with blood cells, while the acidic alpha-keratose caused excessive aggregation.

Samples of acidic and basic alpha-keratose, unfractionated alpha+gamma-kerateines, unfractionated alpha+gamma-keratose, and beta-keratose (derived from cuticle) were prepared at approximately 4 w/v % and pH 7.4 in phosphate buffered saline (PBS). Samples were tested for viscosity and RBC aggregation. These results are shown in Table 1:

TABLE 1

Results of viscosity and RBC aggregation tests on keratin solutions.
Fluid formulations were prepared at approximately 4 w/v % in PBS at
pH 7.4 and tested with human whole blood at a ratio of 1:1.

| Sample Description | Viscosity (centipoise) | RBC Aggregation* |
|---|---|---|
| acidic alpha-keratose (1X AIEx) | 5.65 | 3 |
| acidic alpha-keratose (2X AIEx) | 19.7 | 5 |
| basic alpha-keratose | 1.57 | 2 |
| alpha + gamma-keratose (hydrolyzed) | 1.12 | 1 |
| alpha + gamma-kerateine (unfractionated) | 1.59 | 2 |

*Degree of aggregation: 1 = none, 5 = high

EXAMPLE 2

Cell Proliferation and Wound Healing in Animal Models

Several in vitro and in vivo studies were conducted to demonstrate the biological activity of keratin biomaterials. They involved the use of keratin proteins derived from human hair using oxidation and reduction reactions to break down the tertiary structure of the cortex and extract soluble proteins according to the following methods.

Keratin biomaterials derived from human hair mediated the growth behavior of skin component cells. In cell culture experiments, certain types of keratins were mitogenic toward fibroblasts and keratinocytes. Keratin-based hydrogels were shown to be capable of passivating chemical and thermal burns in a mouse and pig model, respectively.

Keratose: Clean, dry hair was cut into small fibers and oxidized with peracetic acid. Free proteins were extracted using a denaturing solution, neutralized, purified by dialysis, concentrated, and isolated by lyophilization. A hydrogel was formed by re-hydration with phosphate buffered saline (PBS).

Kerateine: Clean, dry hair was cut into small fibers and reduced with thioglycolic acid. Free proteins were extracted using a denaturing solution, dialyzed, neutralized, and concentrated. Upon concentration, a viscous hydrogel formed upon exposure to air.

Figure 1B:
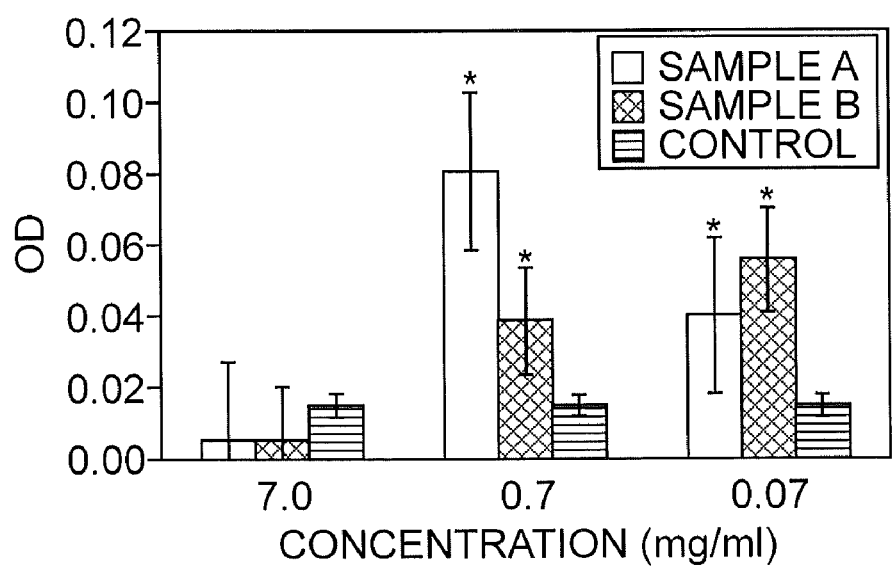

Cell proliferation: Keratose powder (unfractionated keratose, alpha+gamma) was dissolved in culture media with and without serum at several concentrations and used to culture human dermal fibroblasts and keratinocytes. The cells had been grown to approximately 50% confluency in serum-containing media and serum starved for 24 hours prior to exposure to the keratin-containing solutions. After 24 hours of culture with the keratin-containing media, cell proliferation was evaluated using a mitochondria metabolic assay (MTT assay). Cell proliferation assays using keratinocytes and fibroblasts showed statistically significant increases in the keratose treated groups (FIG. 1).

Figure 2:
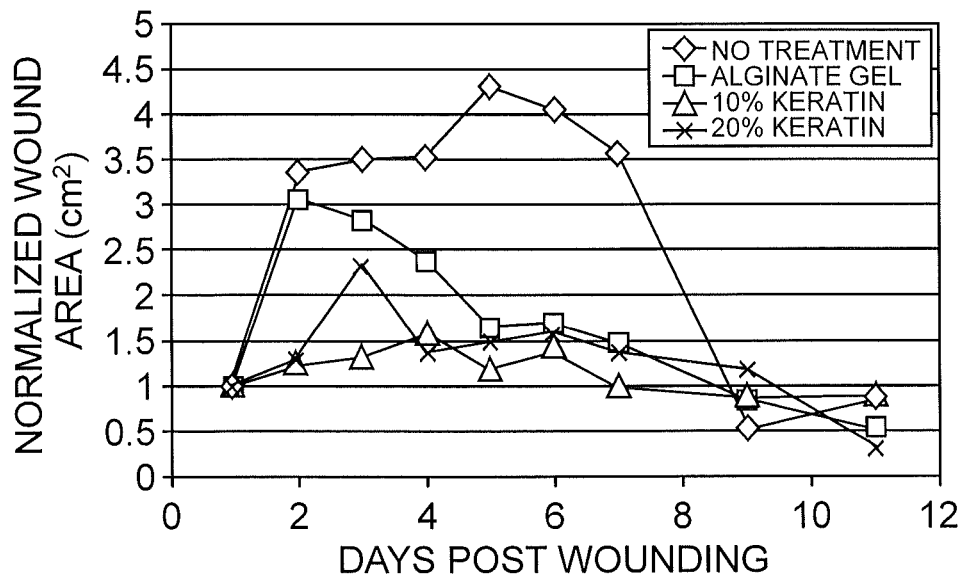
FIG. 2. Changes in chemical burn wound area over time. Mice treated with phenol to induce a chemical burn experience a passivation of the wound site such that the normal course of wound growth does not occur.

Wound healing: Immune competent mice were de-haired and a chemical burn induced between the shoulders using phenol. The wounds were treated after 20 minutes with a keratin hydrogel and occlusive bandage. The keratin used was unfractionated (alpha+gamma) keratose. Dressings were changed every three days for up to 10 days. Digital photos of the wounds were taken and animals sacrificed at various time points so that the wound area could be excised for histological examination. Wound healing studies in mice demonstrated an interesting passivation of the chemical burn. FIG. 2 shows the normal course of wound progression in a wound treated only with an occlusive dressing as initially increasing in wound area. This is due to destruction of vascular support of the peripheral tissue followed thereafter by necrosis at the wound margins. The result is a characteristic growth of the wound area. In the keratin treated groups, however, the trend was toward stabilization of the wound area at the onset of injury. This is thought to be due to a protective mechanism that limits morbidity, and/or rapid induction of angiogenesis that counteracts the initial loss of vascular support.

Figure 3:
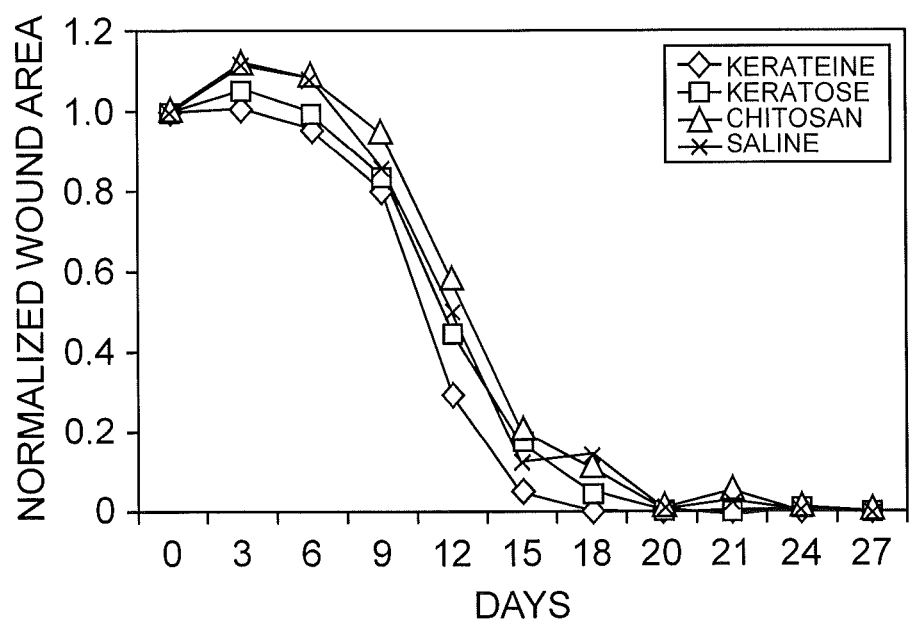
FIG. 3. Burn wound area in pigs. Wound areas were determined by digital image analysis and normalized to the day zero values. Wounds treated with keratin gels did not increase in area appreciably in the first several days and healed more quickly than controls.

In a subsequent large animal study, pigs were cleaned and shaved, and a series of deep partial thickness burns were produced along the dorsal midline using a heated brass block. Wounds were treated every three days for up to 27 days. Keratins used were unfractionated (alpha+gamma) keratose and unfractionated (alpha+gamma) kerateine. Digital photos of the wounds were taken and animals sacrificed at various time points so that the wound area could be excised for histological examination. In this large animal study, the previous findings from the mouse study detailed above were confirmed, with the keratin treatments suppressing wound growth and accelerating healing compared to control groups (FIG. 3).

EXAMPLE 3

Control of Bleeding in an Animal Model

The hemostatic potential of keratin gel was evaluated in a modestly challenging animal model. The keratin gel comprised unfractionated kerateine (alpha+gamma). Liver injuries are notoriously problematic as both the size of the liver and of the wound increase. This rabbit model can produce both profuse and lethal hemorrhage. Controlled liver transection was used as a means to establish a consistent set of conditions that would result in exsanguination in the absence of treatment (negative control), yet provide for the recovery of test animals when a conventional hemostat was applied (positive control). It should be noted that the hemostats used as positive controls in this study are indicated for topical wounds and require concomitant pressure; they were applied without compression in this study. This was done to avoid the confounding contribution compression would add as it was not used with the keratin gel.

A total of 16 New Zealand rabbits (3.7 kg average) were used in this study. The animals received a standardized liver injury that consisted of transection of approximately one third of the left central lobe and were then randomized into one of four groups. Four animals served as negative controls and received no treatment, four animals received treatment with QuikClot® hemostatic agent, four animals were treated with HemCon® hemostatic bandage, and four animals were treated with keratin gel. No resuscitation fluids were given and all animals were closely monitored during surgery. After one hour the surgical wound was closed and the animals transferred to the housing facility. All surviving animals were sacrificed after 72 hours. At the time of sacrifice, liver tissue was retrieved for histological analysis.

Surgeries and Postoperative Treatment. All procedures were performed in accordance with Wake Forest University's Animal Care and Use Committee guidelines, which encompass regulatory and accreditation agencies' guidelines. The animals were weighed immediately before surgery. All animals were sedated using a combination of Ketamine 10 mg/kg and Xylazine 4 mg/kg through an intramuscular injection, intubated and maintained on 2-3% Isoflurane for the remainder of the procedure. The animals were then placed in a supine position, shaved and connected to the monitoring devices. All animals were connected to ECG leads, pulse oximeter cuff on the tail, and an intra-esophageal probe for temperature monitoring. After sterile prepping and draping, the abdominal incision was performed and the liver exposed. Prior to the liver injury, the abdominal aorta of the animals was exposed and canulated using a 23 gauge needle connected to a pressure transducer (Lab-stat, ADInstruments Pty. Ltd. Castle Hill, Australia) which in turn was connected to a PowerLab®(ADInstruments) system for data acquisition. The mean arterial pressure (MAP) was recorded continuously throughout the procedure. All animals were monitored for several minutes and assured to be in a stable state prior to liver injury. The median lobe of the liver was used for the injury due to its ample size and easy accessibility.

Preliminary data during model development showed that a consistent liver injury cross sectional area could be created that resulted in death when left untreated, but that when treated with a control material could rescue the animal. A 2.0 $cm^2$ surface area ring was used to inflict a consistent sized injury to the liver by pulling the left central lobe through the ring and cutting immediately adjacent to the ring with a surgical blade. The MAP, temperature, heart rate, $O_2$ saturation, and shed blood were recorded throughout the procedure at 30 seconds, 5, 15, 30, 45 and 60 minutes, Shed blood was measured at each time point using pre-weighed sterile surgical gauze that was placed under the liver injury. In addition, blood samples were taken for CBC through an ear vein.

All animals were randomized into the previously mentioned four experimental groups. The negative control group did not receive any treatment and the time of death was recorded in minutes after infliction of the injury. As for the other experimental groups, the treatment was administered at the 5 minute time point unless the MAP fell to half of the starting value. For standardization, the hemostatic materials applied were measured or weighed. The keratin gel does not require compression so no compression was used in any of the other treatment groups so as not to confound the results. In the HemCon® hemostatic bandage treatment group, a 4.5×2.5 cm piece of bandage that was placed on the bleeding surface of the liver throughout the procedure and was removed prior to closure. In the QuikClot® hemostatic agent treated group, 2.5 grams of autoclave sterilized material per animal was used. The material was spread on the bleeding surface and was left after closure in the surviving animals. In the case of the keratin treatment group, 2 ml of the gel was used per animal. Sterile keratin gel was applied to the bleeding surface through a 1 ml syringe.

The keratin was also left in place after closure of the animals. These parameters were determined during initial model development based on complete coverage of the wound site. For the surviving animals, the monitoring continued for 60 minutes, after which the animal was considered to have survived the initial trauma and the bleeding stopped. The animals that were treated with HemCon® hemostatic bandage had to undergo removal of the material since it could not be left intraabdominally as indicated by the manufacturer. The aortic cannula was removed and hemostasis established at the insertion site. No aortic bleeding was observed in any animal at necropsy. The fascia and skin of the abdomen was closed in two layers. After complete closure of the abdomen, the animals were allowed to recover and transported to the housing facility where they were monitored every 15 minutes until complete recovery from anesthesia, then three times per day thereafter for the following three days. Blood samples were taken from all surviving animals every day for CBC analysis. Upon sacrifice at the 72 hour time point, the liver of each animal was harvested for histological evaluation.

All presented data is expressed as averages and the corresponding standard deviations. For statistical analysis, SPSS v.11 (SPSS Inc, Chicago, Ill.) was used. Outliers were defined as having a z-score larger then +3.0 or smaller then −3.0 using a modified z-score (median of the absolute deviation). Data at all time points were analyzed by one-way analysis of variance (ANOVA). If significant F values were found, the groups were further analyzed by Fischer's Least Significant Difference Test (LSD). An alpha of $p<0.05$ was considered significant. The probability of a Type I error was minimized by limiting comparisons; only negative control versus the 3 treatment groups were performed. In order to compensate for bias generated by early drop out of dead animals (i.e. animals that exsanguinated before the end of the 60 minute operative period), polynomial regression to known pathologic endpoints was used to estimate values during the first 60 minutes. For the percent blood loss graphical data (FIG. 5) where statistical relevance was reached with some groups, values are expressed as means with their corresponding standard error.

Figure 4:
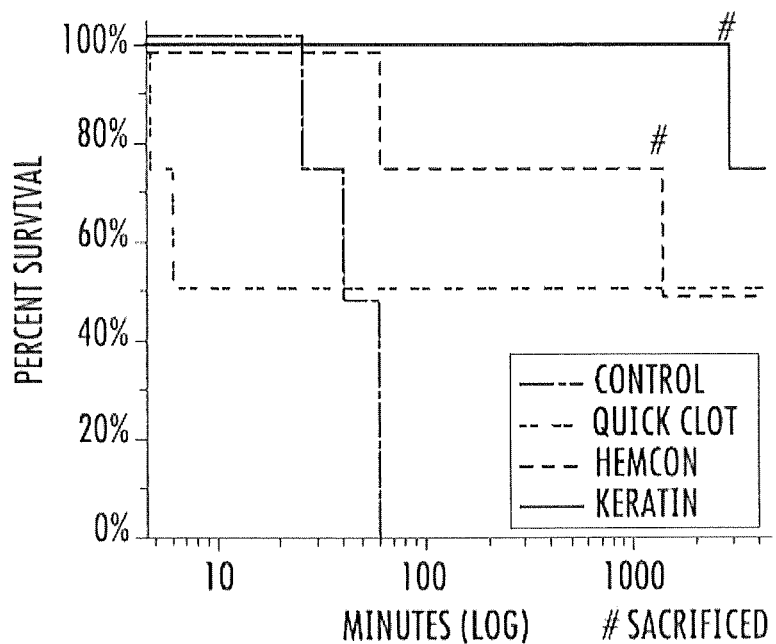
FIG. 4. Kaplan-Mayer Survival Graph: Time is presented in minutes on a logarithmic scale. All animals in the control group died within 60 minutes. One animal from the keratin and one from the HemCon® hemostatic bandage group was sacrificed upon recommendation of the animal care staff. Overall, keratin outperformed the other groups with only one death compared with 2 deaths in the QuikClot® hemostatic agent and HemCon® hemostatic bandage groups.

Negative control animals (i.e. no treatment), as expected, exsanguinated within the 60 minute operative period (31±19 minutes). Two animals in the QuikClot® hemostatic agent group and one in the HemCon® hemostatic bandage group did not survive beyond the initial 60 minute operative period. Also in the HemCon® hemostatic bandage group, one animal was euthanized 24 hours post-op on the advice of the veterinary staff. This animal was not ambulatory and could not eat or drink. One animal in the keratin group was also sacrificed at 48 hours. Although the animal was moving freely in its cage, it was not eating or drinking. At necropsy, these animals showed no evidence of additional bleeding after the operative period. All other surviving animals recovered without incident, were freely moving in their cages within 24 hours, and had normal CBC by 72 hours (data not shown). A summary of the survival data is shown in FIG. 4.

Mean Arterial Pressure. The mean arterial pressure (MAP) was recorded using a 23 gauge needle placed into the lower part of the abdominal aorta. The needle was connected to a PE 50 tube, which in turn was connected to a pressure transducer (Lab-stat) that was connected to a PowerLab system for pressure recording. The MAP was continuously monitored during the entire course of the procedure or until the death of the animal. To further evaluate the significance of a change in MAP and heart rate, shock index was used. Shock index is a well established clinical scoring system for fast assessment of trauma patients. The modified shock index was calculated by dividing heart rate by MAP (mmHg).

Figure 6:
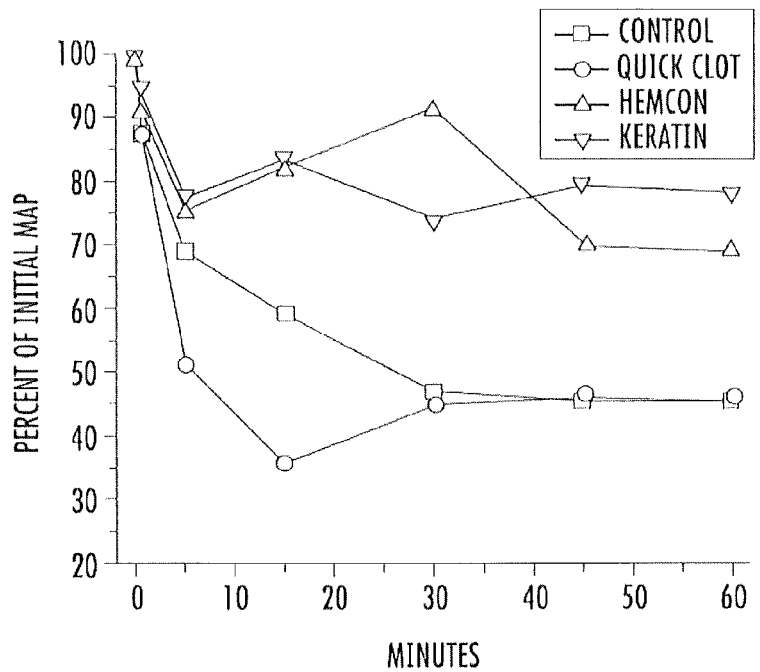
FIG. 6. Mean Arterial Pressure (MAP): Blood pressure is expressed in percentage of initial pressure. The negative control and QuikClot® hemostatic agent groups showed a steep drop in pressure to 40% of initial MAP. Animals treated with keratin or HemCon® hemostatic bandage were able to stabilize the MAP around 80% of initial pressure. These differences were not statistically different compared to the control group.

The mean arterial pressure in the abdominal aorta was recorded for 60 minutes. Animals in the keratin and HemCon® hemostatic bandage group were able to achieve stable MAPs after 5 minutes at 75% of the starting value. The QuikClot® hemostatic agent and control groups failed to stabilize MAP and dropped to 45% of the starting value after 60 minutes (FIG. 6). However, these data did not reach statistical significance between groups.

Figure 7:
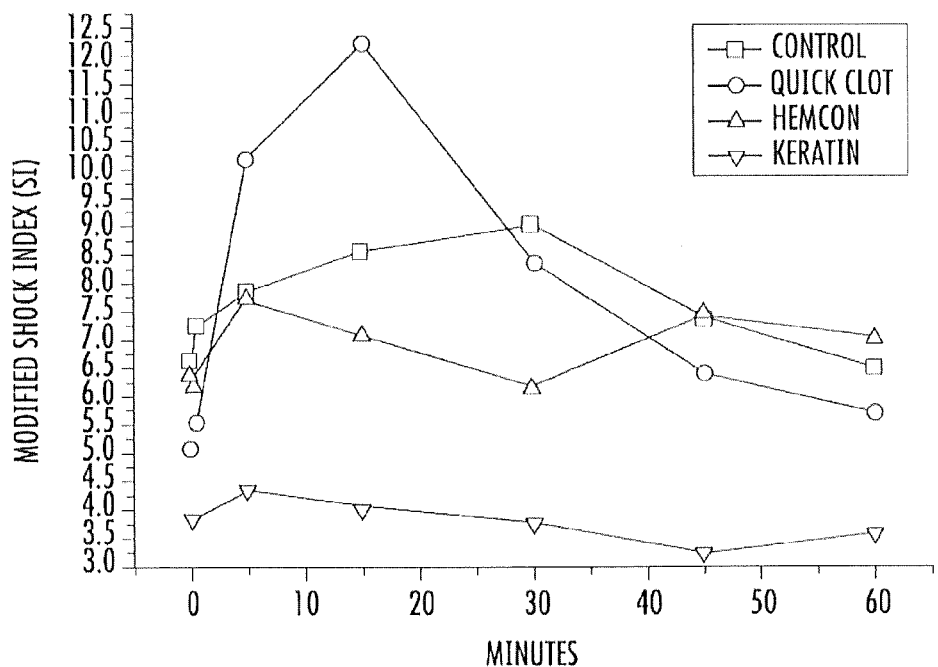
FIG. 7. Shock Index (SI): The modified shock index was calculated by dividing heart rate by MAP. This index is clinically used to assess the severity of a shock, with low values being better. The animals in the keratin group showed compensated low values over the entire study period, while QuikClot® hemostatic agent and HemCon® hemostatic bandage groups had similar values as the negative control. There was no statistical significance between the groups.

The shock index (SI), a predictive score grading system for the severity of blood loss, showed a beneficial outcome for the keratin group with low values throughout the first 60 minutes (FIG. 7). The high values of QuikClot® hemostatic agent matched with two early deaths during the first 20 minutes of observation supporting the predictive nature of this measure. Although a trend was noted, these data did not reach statistical significance in the present study.

Temperature, ECG and Heart Rate. The central temperature was recorded with an esophageal probe connected to the surgery room monitor. The temperature of the animal was continuously monitored throughout the procedure and recorded at the previously mentioned time points. The ECG and heart rate were monitored using a three lead system connected to the surgery room monitor and was maintained throughout the entire procedure. Flat line or irregular electrical activity with electrical mechanical dissociation was used to define the time of death.

The liver damage model employed in this study represented severe trauma with significant, rapid blood loss. The liver transection produced a lethal injury, typically involving one or two large vessels of approximately 1 mm diameter and several in the 0.5 to 1.0 mm diameter ranges. The severity of the injury was such that untreated rabbits all exsanguinated within the 60 minute operative period. None of the animals were able to compensate for loss of blood volume with an increase in heart rate. All animals showed a comparable decrease from 263 bpm to 188 bpm after 30 minutes and 154 bpm after one hour. There were no statistically significance differences between the groups. However, the keratin group showed a trend toward compensation and recovery with an increase in heart rate in the second half of the surgical period from 30 min to 60 min. The temperature of all animals dropped in a similar fashion with a step drop of 0.8° C. in the first 5 minutes and a total of 2.7° C. over 60 minutes. There was no statistically significant difference between the experimental groups.

Shed Blood. Shed blood was measured by weight after subtracting the weight of the pre-weighed gauze. Weights were recorded at each time point and fresh gauze placed under the liver injury. The shed blood was represented as a percent of the original body weight for each animal. CBC was determined from samples taken from an ear vein on a HEMAVet® multi-species hematology system (Model 950FS, Drew Scientific, Dallas, Tex.).

Figure 5:
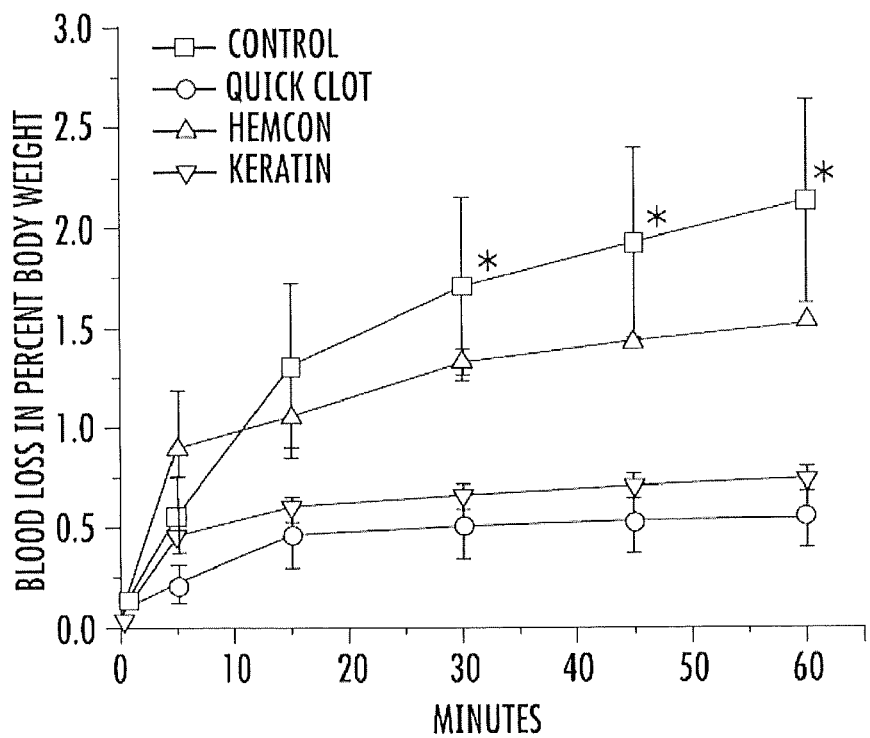
FIG. 5. Shed Blood: Blood loss is normalized to body weight and expressed as percentage of body weight. Keratin and QuikClot® hemostatic agent groups lost significantly (*) less blood than the control and HemCon® hemostatic bandage groups.

Blood loss was measured by weighing the surgical gauze placed below the injured liver lobe. The blood loss was expressed as percentage of starting body weight. As expected in uncontrolled hemorrhage studies, all animals showed an initial phase of profuse bleeding followed by a linear phase with a lower bleeding rate, as MAP falls (FIG. 5). A comparison of the keratin and QuikClot® hemostatic agent groups to the negative controls shows a significantly decreased amount of blood loss at the 30, 45, and 60 minute time points (p values for keratin vs. negative control were 0.018, 0.011 and 0.007; p values for QuikClot® hemostatic agent vs. negative control were 0.009, 0.005 and 0.004, respectively).

As one would expect, the survivability of the animals appeared to be dependent on the vascular anatomy at the injury site, which was not consistent from animal to animal even though the total surface area transected was controlled. When a single very large bleeder (>1 mm), or multiple large bleeders (>2 to 3 in the 1 m size range) were encountered within the injury area, the animal's chance of survival was negligible in the QuikClot® hemostatic agent and HemCon® hemostatic bandage groups. In the QuikClot® hemostatic agent group in particular, a single very large bleeder or an excess of 2 to 3 large bleeders would ensure lethality. It should be noted however, that when used according to manufacturer's instructions with concomitant pressure, other studies have shown better survival rates using QuikClot® hemostatic agent and HemCon® hemostatic bandage. In all cases of treatment with keratin gel, which was also used without any compression, the animals survived for at least 24 hours, regardless of the size of the severed vessels. Although a small number of animals were used in all test groups (n=4), these outcomes are encouraging.

The keratin hemostatic gel consistently performed well by each outcome measure, particularly shed blood volume, MAP, and (importantly) survival. One particularly distinguishing outcome was shock index. In most cases of hemorrhage, cardiac output is increased to compensate for the drop in blood pressure. Once this mechanism takes over, the value of shock index increases rapidly and survivability becomes doubtful. Remarkably, the shock index in the keratin treatment group remained the lowest of all the materials tested, consistent with early effective hemostasis.

Histology. A tissue sample including the damaged liver surface was removed from each animal within one hour of euthanasia. Each sample was placed in Tissue-Tek® O.C.T. Compound 4583 (Sakura®) and frozen in liquid nitrogen. The frozen blocks were sectioned into 8 μm slices using a cryostat (Model CM 1850, Leica Microsystems, Bannockburn, Ill.) to include the transected portion of the liver and mounted onto microscope slides. The slides were fixed and stained with Hematoxylin and Eosin (H&E). Technical difficulties in sectioning arose with both the QuikClot® hemostatic agent and the HemCon® hemostatic bandage sections. The brittle QuikClot® hemostatic agent made level sectioning difficult and created voids in the sections. The HemCon® hemostatic bandage was removed before abdominal closure and therefore the clotted blood was only partially visible. Digital images were taken (Zeiss Axio Imager M1 Microscope, Carl Zeiss, Thornwood, N.Y.) at varying magnifications to observe the interactions between the hemostat and the damaged area of the liver. A magnification of 100× showed the overall response of the tissue, while magnifications of 200× and 400× were used to visualize the cellular response.

Figure 8:
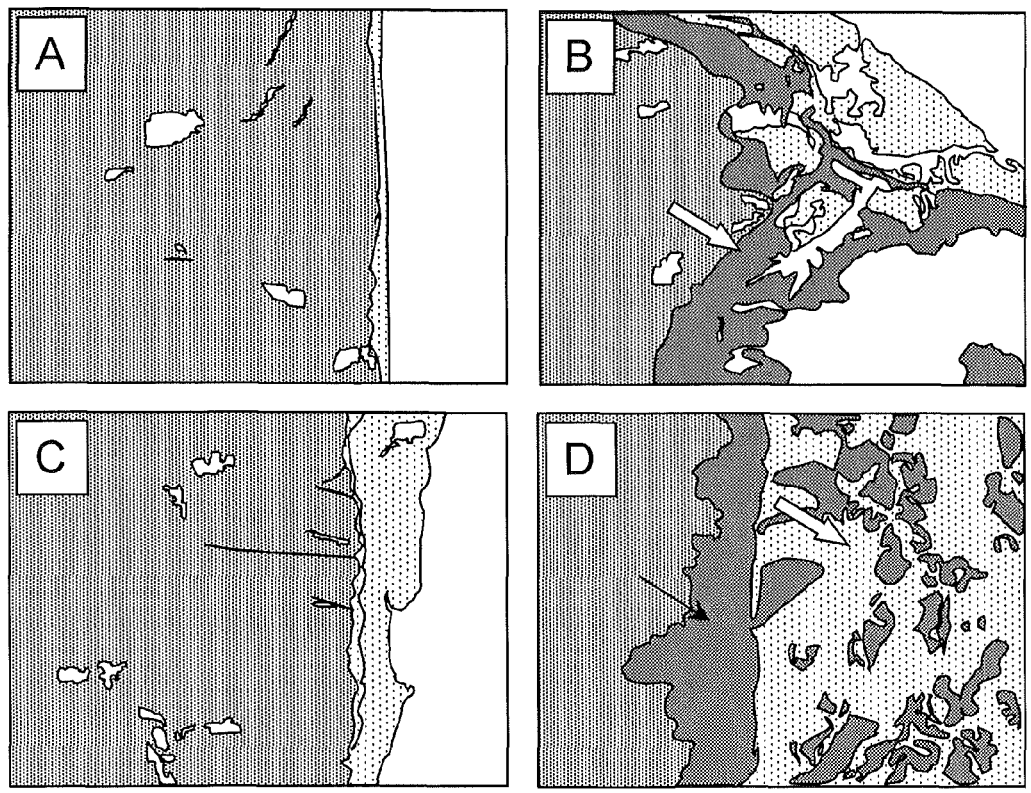
FIG. 8. Histological Assessment: Representative tissue sections stained with hematoxylin and eosin, 50×. A) The negative control group shows signs of poor perfusion with wide and empty sinusoids. The surface is lacking a functional blood clot. B) The surface of the QuikClot® hemostatic agent treated samples shows an area of necrosis (arrow) and clotting. Only minimal cellular infiltration and tissue regeneration is visible. The void areas represent the removed QuikClot® hemostatic agent granules. C) Tissue samples from HemCon® hemostatic bandage treated animals showed patchy areas of adherent clotted blood, where there was a low level of cellular infiltration. D) Liver samples from animals treated with keratin show a thick layer of keratin biomaterial attached to the injured surface. There are signs of excellent biocompatibility with a high cellular activity and the formation of early granular tissue (large arrow) in the spaces between the keratin. Further, there is a high level of direct contact of hepatocytes with the keratin biomaterial (small arrow).
Figure 9:
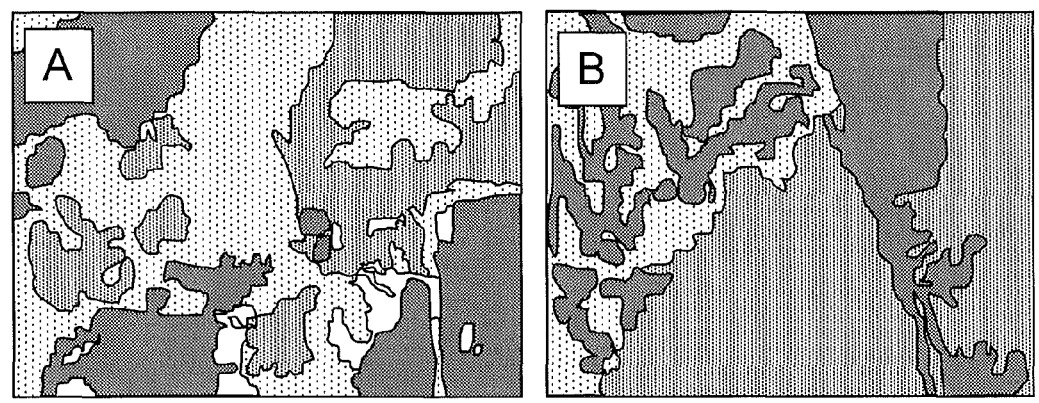
FIG. 9. Keratin Treated Group, High Magnification: A) Formation of early granulation-like tissue within the spaces of the keratin gel, 200×. B) Interface between keratin gel and liver tissue showing integration of the biomaterial and tissue, and early cellular infiltration, 400×.

The transected liver surfaces were examined by light microscopy of H&E stained sections. The negative control group showed a clean cut with no tissue response or necrosis (FIG. 8A). Moreover, no functional clotting was observed with little thrombus adhered to the surface. The QuikClot® hemostatic agent samples were difficult to process due to the presence of this hard, granular zeolite in the clot. Histology revealed necrotic tissue mixed with blood clots (FIG. 8B). The transparent areas represent QuikClot® hemostatic agent particles removed during processing. The HemCon® hemostatic bandage group showed some areas with clotted blood and adjacent cellular infiltration (FIG. 8C). Since the HemCon®hemostatic bandage was removed after 60 minutes, most of the liver surfaces had only a thin layer of blood clots. The keratin group showed a thick layer of biomaterial attached to the damaged liver surface (FIG. 8D). Granulation-like tissue with cellular infiltration had formed in the pores of the keratin biomaterial gel (FIG. 9).

The keratin hemostatic gel was adherent to the tissue and hydrophilic. When deposited onto the bleeding surface of the liver it was sufficiently adhesive to not be washed away, even in the presence of profuse bleeding. The gel absorbed fluid from the blood and became even more adherent within a few minutes of administration. Clotting and adherence was almost instantaneous with contact. Interestingly, the keratin gel formed a thick seal of granulation-like tissue over the wound site by 72 hours. Upon inspection of histological sections, 3 days after injury host cells could be seen infiltrating the gel. It is believed that the keratin gel used in these experiments serves two purposes. First, contact of the gel with whole blood instigates thrombus formation, probably through platelet activation or concentration of clotting factors. Second, the adherent gel forms a physical seal of the wound site and provides a porous scaffold for cell infiltration and granulation-like tissue formation, much like clotted blood.

The foregoing is illustrative of the present invention, and is not to be construed as limiting thereof. The invention is defined by the following claims, with equivalents of the claims to be included therein.

That which is claimed is:

1. A surgical or paramedic aid, comprising:
   a solid, physiologically acceptable substrate; and
   a composition comprising a keratin derivative on said substrate,
   wherein said keratin derivative is at least 80% by weight of acidic alpha kerateine.

2. The surgical or paramedic aid according to claim 1, wherein said substrate is selected from the group consisting of sponges, packings, wound dressings, sutures, fabrics, and prosthetic devices.

3. The surgical or paramedic aid according to claim 1, wherein said surgical or paramedic aid is sterile, and wherein said surgical or paramedic aid is packaged in a sterile container.

4. The surgical or paramedic aid according to claim 1, wherein said acidic alpha kerateine is produced by the process of fractionating a mixture comprising acidic and basic alpha kerateine by ion exchange chromatography.

5. A surgical or paramedic aid, comprising:
   a solid, physiologically acceptable substrate; and
   a composition comprising a keratin derivative on said substrate,
   wherein said keratin derivative is at least 80% by weight of acidic alpha keratose.

6. The surgical or paramedic aid according to claim 5, wherein said substrate is selected from the group consisting of sponges, packings, wound dressing, sutures, fabrics, and prosthetic devices.

7. The surgical or paramedic aid according to claim 5, wherein said surgical or paramedic aid is sterile, and wherein said surgical or paramedic aid is packaged in a sterile container.

8. The surgical or paramedic aid according to claim 5, wherein said acidic alpha keratose is produced by the process of fractionating a mixture comprising acidic and basic alpha keratose by ion exchange chromatography.

9. A kit comprising:
   a) a composition comprising a keratin derivative, wherein said keratin derivative is at least 80% by weight of acidic alpha kerateine; and
   b) a container in which said keratin derivative is packaged in said container in sterile form.

10. The kit of claim 9, wherein said keratin derivative is provided in hydrated or dehydrated form.

11. The kit of claim 9, wherein said container comprises a foil container.

12. The kit of claim 9, wherein said container is vacuum-packed.

13. The kit of claim 9, wherein said keratin derivative comprises a single unit dose.

14. The kit of claim 9, wherein said keratin derivative comprises 0.5 to 200 grams of dehydrated acidic alpha kerateine.

15. The kit of claim 9, wherein said keratin derivative comprises 0.5 to 200 milliliters of hydrated acidic alpha kerateine.

16. The kit of claim 9, further comprising a physiologically acceptable substrate.

17. The kit of claim 16, wherein said substrate is sterile, and wherein said substrate is packaged in said container in sterile form.

18. The kit of claim 16, wherein said substrate is selected from the group consisting of sponges, packings, wound dressings, sutures, fabrics, and prosthetic devices.

19. A kit comprising:
   a) a composition comprising a keratin derivative, wherein said keratin derivative is at least 80% by weight of acidic alpha keratose; and
   b) a container in which said keratin derivative is packaged in said container is sterile form.

20. The kit of claim 19, wherein said keratin derivative is provided in hydrated or dehydrated form.

21. The kit of claim 19, wherein said container comprises a foil container.

22. The kit of claim 19, wherein said container is vacuum-packed.

23. The kit of claim 19, wherein said keratin derivative comprises a single unit dose.

24. The kit of claim 19, wherein said keratin derivative comprises 0.5 to 200 grams of dehydrated acidic alpha keratose.

25. The kit of claim 19, wherein said keratin derivative comprises 0.5 to 200 milliliters of hydrated acidic alpha keratose.

26. The kit of claim 19, further comprising a physiologically acceptable substrate.

27. The kit of claim 26, wherein said substrate is sterile, and wherein said substrate is packaged in said container in sterile form.

28. The kit of claim 26, wherein said substrate is selected from the group consisting of sponges, packings, wound dressings, sutures, fabrics, and prosthetic devices.

* * * * *

UNITED STATES PATENT AND TRADEMARK OFFICE
CERTIFICATE OF CORRECTION

PATENT NO. : 8,258,093 B2  
APPLICATION NO. : 13/241552  
DATED : September 4, 2012  
INVENTOR(S) : Van Dyke Page 1 of 1

It is certified that error appears in the above-identified patent and that said Letters Patent is hereby corrected as shown below:

On the Title Page: Second Item (60), Line 4:

Please add -- provisional application number 60/912,265 filed on April 17, 2007 --

In the Claims:
Column 30, Claim 19, Line 36: Please correct "in said container is sterile form."
to read -- in said container in sterile form. --

Signed and Sealed this
Fifth Day of February, 2013

Teresa Stanek Rea
*Acting Director of the United States Patent and Trademark Office*